US012788997B2

(12) United States Patent
Formosa et al.

(10) Patent No.: US 12,788,997 B2
(45) Date of Patent: Nov. 10, 2026

(54) IMPLANTABLE MEDICAL LEAD WITH SHIELD

(71) Applicant: Medtronic, Inc., Minneapolis, MN (US)

(72) Inventors: Elizabeth K. Formosa, Santa Clara, CA (US); Kevin R. Seifert, Forest Lake, MN (US); Vladimir P. Nikolski, San Diego, CA (US); Mark T. Marshall, Cape Coral, FL (US); Blaine A. Schneider, Corcoran, MN (US)

(73) Assignee: Medtronic, Inc., Minneapolis, MN (US)

( * ) Notice: Subject to any disclaimer, the term of this patent is extended or adjusted under 35 U.S.C. 154(b) by 148 days.

(21) Appl. No.: 18/845,758

(22) PCT Filed: Mar. 10, 2023

(86) PCT No.: PCT/US2023/064147

§ 371 (c)(1),
(2) Date: Sep. 10, 2024

(87) PCT Pub. No.: WO2023/173092

PCT Pub. Date: Sep. 14, 2023

(65) Prior Publication Data

US 2025/0186788 A1 Jun. 12, 2025

Related U.S. Application Data

(60) Provisional application No. 63/269,191, filed on Mar. 11, 2022.

(51) Int. Cl.

| | |
|---|---|
| ***A61N 1/37*** | (2006.01) |
| ***A61N 1/05*** | (2006.01) |
| ***A61N 1/375*** | (2006.01) |

(52) U.S. Cl.
CPC ....... *A61N 1/37512* (2017.08); *A61N 1/0563* (2013.01)

(58) Field of Classification Search
CPC .. A61N 1/0504; A61N 1/0563; A61N 1/0587; A61N 1/37512; A61N 1/0502;
(Continued)

(56) References Cited

U.S. PATENT DOCUMENTS

| | | | |
|---|---|---|---|
| 5,327,909 | A | 7/1994 | Kiser et al. |
| 5,683,443 | A | 11/1997 | Munshi et al. |

(Continued)

FOREIGN PATENT DOCUMENTS

| | | | |
|---|---|---|---|
| CA | 2400363 | A1 | 8/2001 |
| WO | 9805289 | A1 | 2/1998 |

(Continued)

OTHER PUBLICATIONS

International Preliminary Report on Patentability from International Application No. PCT/US2023/064147 dated Sep. 10, 2024, 4 pp.

(Continued)

*Primary Examiner* — Amanda K Hulbert
(74) *Attorney, Agent, or Firm* — Shumaker & Sieffert, P.A.

(57) ABSTRACT

An example implantable medical lead includes a first defibrillation electrode and a second, defibrillation electrode, the first and second, defibrillation electrodes configured to deliver first electrical therapy comprising anti tachyarrhythmia shocks. The implantable medical lead also includes a pace electrode disposed longitudinally between the first defibrillation electrode and the second defibrillation electrode, the pace electrode configured to deliver a pacing pulse that generates an electric field proximate to the pace electrode. The implantable medical lead further includes an inflatable shield disposed over a portion of an outer surface (Continued)

of the pace electrode, wherein the inflatable shield is configured to extend laterally away from the pace electrode upon inflation, wherein the inflatable shield is configured to impede an electric field of at least, one of the first and second the electrical therapies in a direction away from a heart of the patient.

20 Claims, 17 Drawing Sheets

(58) Field of Classification Search
CPC ...... A61N 1/0565; A61N 1/362; A61N 1/375; A61N 1/39622
See application file for complete search history.

(56) References Cited

U.S. PATENT DOCUMENTS

| | | | |
|---|---|---|---|
| 6,405,091 B1 | 6/2002 | Vachon et al. | |
| 6,699,259 B2 | 3/2004 | Fogarty et al. | |
| 7,765,015 B2 | 7/2010 | Johnson et al. | |
| 9,604,053 B2 | 3/2017 | Kaplan et al. | |
| 10,850,067 B2 | 12/2020 | Reddy et al. | |
| 2003/0144719 A1 | 7/2003 | Zeijlemaker | |
| 2007/0073218 A1 | 3/2007 | Lau et al. | |
| 2007/0239244 A1 | 10/2007 | Morgan et al. | |
| 2013/0013045 A1* | 1/2013 | Soltis | A61N 1/0558 607/118 |
| 2014/0194965 A1 | 7/2014 | Osypka | |
| 2015/0374991 A1 | 12/2015 | Morris et al. | |
| 2016/0158567 A1* | 6/2016 | Marshall | A61N 1/39622 607/116 |
| 2017/0304019 A1 | 10/2017 | Sanghera et al. | |
| 2017/0354365 A1 | 12/2017 | Zhou | |
| 2018/0133458 A1 | 5/2018 | Foster et al. | |
| 2018/0326202 A1 | 11/2018 | McCabe et al. | |
| 2019/0117972 A1 | 4/2019 | Schmidt et al. | |
| 2019/0186702 A1 | 6/2019 | Masson | |
| 2019/0329060 A1 | 10/2019 | De Kock et al. | |
| 2020/0297993 A1 | 9/2020 | Marshall et al. | |
| 2021/0268297 A1 | 9/2021 | Nikolski et al. | |

FOREIGN PATENT DOCUMENTS

| | | |
|---|---|---|
| WO | 2004002288 A1 | 1/2004 |
| WO | 2008088967 A1 | 7/2008 |
| WO | 2009135075 A1 | 11/2009 |
| WO | 2013029587 A1 | 3/2013 |

OTHER PUBLICATIONS

International Search Report and Written Opinion of International Application No. PCT/US2023/064147 dated Jun. 22, 2023, 6 pp.
U.S. Appl. No. 18/836,903, filed Mar. 10, 2023, naming inventors Nikolski et al.

* cited by examiner

IMPLANTABLE MEDICAL LEAD WITH SHIELD

This application is a national phase entry of International Application PCT/US2023/064147, filed Mar. 10, 2023, which claims the benefit of priority from U.S. Provisional Patent Application No. 63/269,191, filed on Mar. 11, 2022, and entitled, "IMPLANTABLE MEDICAL LEAD WITH SHIELD," the entire content of each of which is incorporated by reference herein.

TECHNICAL FIELD

The present application relates to implantable medical leads and, more particularly, implantable medical leads with one or more structures to reduce the likelihood of stimulation of unintended tissue.

BACKGROUND

Malignant tachyarrhythmia, for example, ventricular fibrillation (VF), is an uncoordinated contraction of the cardiac muscle of the ventricles in the heart, and is the most commonly identified arrhythmia in cardiac arrest patients. If this arrhythmia continues for more than a few seconds, it may result in cardiogenic shock and cessation of effective blood circulation. As a consequence, sudden cardiac death (SCD) may result in a matter of minutes.

In patients with a high risk of VF, the use of implantable systems, such as an implantable cardioverter defibrillator (ICD) system has been shown to be beneficial at preventing SCD. Implantable systems, such as pacemakers with or without cardioversion or defibrillation capabilities, may also treat other cardiac dysfunction, such as bradycardia and heart failure. Such implantable systems may include electrical devices configured to deliver therapy via electrodes. Therapy may include shocks and/or anti-tachycardia pacing (ATP). The implantable systems may also be configured to deliver cardiac pacing to, for example, treat bradyarrhythmia or for cardiac resynchronization therapy (CRT).

An implantable system may include one or more implantable medical leads. A distal portion of an implantable medical lead may include one or more electrodes, and may be positioned at a target location within the patient for delivery of electrical therapy and/or electrical sensing via the electrodes. A proximal end of the lead may be coupled to the implantable system. The implantable system may also include one or more housing electrodes, which are sometimes referred to as can electrodes, for delivery of therapy and/or sensing.

Owing to the inherent surgical risks in attaching and replacing implantable medical leads directly within or on the heart, subcutaneous implantable systems have been devised, in which the implantable system and leads are located subcutaneously outside of the thorax. It has also been proposed that the distal portion of a lead of an implantable system may be implanted within the thorax, but not in contact with the heart, e.g., substernally. Additionally, it has been proposed to implant the distal portion of a lead of an implantable system within an extracardiac vessel that is within the thorax, such as the internal thoracic vein (ITV), the intercostal veins, the superior epigastric vein, or the azygos, hemiazygos, and accessory hemiazygos veins.

Implantable medical leads are also used to deliver therapies to tissues other than the heart. Implantable medical leads may be used to position one or more electrodes within or near target nerves, muscles, or organs to deliver electrical stimulation to such tissues. As examples, implantable medical leads may be positioned in the epidural space to deliver spinal cord stimulation, or proximate to other nerves, such as pelvic nerves or renal nerves, to deliver neurostimulation to the nerves.

SUMMARY

Relative to electrodes on or within the heart, delivery of pacing pulses or defibrillation using electrodes of extravascular leads may require higher energy levels to capture and/or defibrillate the heart. Furthermore, conventional pace electrodes placed extravascularly may direct a significant portion of the electrical field produced by a pacing pulse away from the heart. The electrical field directed away from the heart may stimulate extracardiac tissue, such as the phrenic nerve, nerve endings in the intercostal regions, or other sensory or motor nerves. These issues may similarly occur when electrodes are implanted within extracardiac vessels within the thorax, such as the ITV, the intercostal veins, the superior epigastric vein, or the azygos, hemiazygos, and accessory hemiazygos veins, or when electrodes are implanted in other extracardiac locations.

This disclosure describes implantable medical leads and implantable systems, such as ICD systems, utilizing the leads. More particularly, this disclosure describes systems including implantable medical leads and expandable shields configured to impede the electric field from the implantable medical lead, e.g., block or reduce the electric field, in a direction from the implantable medical lead and the heart, e.g., an anterior direction. In this manner, the shield may reduce the likelihood that unintended patient tissue is stimulated. Additionally, the shield may be deliverable via a delivery tool. For example, the shield may be unexpanded, e.g., compressed, deflated, and the like, so as to be compatible with a lumen of a delivery tool such as an introducer and to be delivered to an intended location within a patient. The configuration of the shield may further improve removal of the shield and/or implantable medical lead. For example, the expandable and compressible shield may be compressed, deflated, and the like, so as to be removable by an introducer tool. In some examples, the shield may be compressed, deflated, and the like, to release from tissue of the patient for removal of the implantable medical lead, or attached to the implantable medical lead to reduce and/or prevent in-growth of tissue and thereby improve removal of the implantable medical lead and shield. Furthermore, the shield may direct the electrical field toward the heart, allowing lower energy level electrical fields to capture the heart than may be required without the shield. Lower energy pacing pulses may also reduce the likelihood that pacing pulses delivered via the pace electrode stimulate extracardiac tissue, and may result is less consumption of the power source of the ICD and, consequently, longer service life for the ICD.

Although described herein primarily in the context of ICD systems, various aspects of the techniques of this disclosure may be applied to implantable systems other than ICD systems, including, but not limited to, bradycardia or CRT pacemaker systems. Accordingly, implantable medical leads having one or more shields may be used in contexts other than that of ICD systems, both cardiac and non-cardiac. As one example, implantable medical leads that have a shield over a portion of a surface of an electrode may be used with an extracardiac pacemaker system without defibrillation capabilities. As another example, implantable medical leads that have a shield over a portion of a surface of an electrode may impede an electrical field resulting from delivery of neurostimulation from the electrode in a direction away from a target nerve. In this manner, the shield may direct the neurostimulation to intended tissue, and reduce the likelihood that the neurostimulation stimulates unintended tissues.

In one example, this disclosure describes an implantable medical lead including: a first defibrillation electrode and a second defibrillation electrode, the first and second defibrillation electrodes configured to deliver a first electrical therapy; a pace electrode disposed longitudinally between the first defibrillation electrode and the second defibrillation electrode, the pace electrode configured to deliver a second electrical therapy comprising pacing pulses; and a shield disposed over a portion of an outer surface of the pace electrode and extending laterally away from the pace electrode, wherein the shield comprises an asymmetric shape about a longitudinal axis of the shield, wherein the shield is configured to impede an electric field of at least one of the first and second electrical therapies in a direction away from a heart of the patient.

In another example, this disclosure describes a method including: positioning an implantable medical lead at an implant location within a patient, wherein the implantable medical lead comprises: a first defibrillation electrode and a second defibrillation electrode, the first and second defibrillation electrodes configured to deliver antitachyarrhythmia shocks, a pace electrode disposed longitudinally between the first defibrillation electrode and the second defibrillation electrode, the pace electrode configured to deliver a pacing pulse that generates an electric field proximate to the pace electrode; and a shield configured to be disposed over a portion of an outer surface of the pace electrode and extending laterally away from the pace electrode in a deployed configuration, wherein the shield comprises an asymmetric shape about a longitudinal axis of the shield in the deployed configuration, wherein the shield is configured to impede an electric field of at least one of the first and second electrical therapies in a direction away from a heart of the patient in the deployed configuration; and expanding, via deploying the implantable medical lead, the shield from a first shape to the asymmetric shape in the deployed configuration.

In another example, this disclosure describes a system including: an implantable medical lead including: a first defibrillation electrode and a second defibrillation electrode, the first and second defibrillation electrodes configured to deliver first electrical therapy; a pace electrode disposed longitudinally between the first defibrillation electrode and the second defibrillation electrode, the pace electrode configured to deliver second electrical therapy comprising pacing pulses; and a shield comprising a substantially flat and single-layered biocompatible material configured to be attached to the implantable medical lead and in a first shape in an undeployed configuration, wherein the shield is configured to be compatible with a delivery tool in the first shape, wherein the shield is configured to be in an asymmetric shape about a longitudinal axis of the shield and disposed over a portion of an outer surface of the pace electrode and extending laterally away from the pace electrode in a deployed configuration, wherein the asymmetric shape, wherein the shield is configured to impede an electric field of at least one of the first and second electrical therapies in a direction away from a heart of the patient in the deployed configuration.

In another example, this disclosure describes an implantable medical lead including: a first defibrillation electrode and a second defibrillation electrode, the first and second defibrillation electrodes configured to deliver first electrical therapy; a pace electrode disposed longitudinally between the first defibrillation electrode and the second defibrillation electrode, the pace electrode configured to deliver a pacing pulse that generates an electric field proximate to the pace electrode; and an inflatable shield disposed at least over a portion of an outer surface of the pace electrode, wherein the inflatable shield is configured to extend laterally away from the pace electrode upon inflation, wherein the inflatable shield is configured to impede an electric field of at least one of the first and second the electrical therapies in a direction away from a heart of the patient.

In another example, this disclosure describes a method including: positioning an implantable medical lead at an implant location within a patient, wherein the implantable medical lead comprises: a first defibrillation electrode and a second defibrillation electrode, the first and second defibrillation electrodes configured to deliver first electrical therapy; a pace electrode disposed longitudinally between the first defibrillation electrode and the second defibrillation electrode, the pace electrode configured to deliver a pacing pulse that generates an electric field proximate to the pace electrode; and an inflatable shield disposed at least over a portion of an outer surface of the pace electrode, wherein the inflatable shield is configured to extend laterally away from the pace electrode in an inflated shape upon inflation, wherein the inflatable shield is configured to impede an electric field of at least one of the first and second the electrical therapies in a direction away from a heart of the patient; and inflating the inflatable shield from a deflated shape to the inflated shape.

In another example, this disclosure describes a system including: an implantable medical lead including: a first defibrillation electrode and a second defibrillation electrode, the first and second defibrillation electrodes configured to deliver first electrical therapy; a pace electrode disposed between the first defibrillation electrode and the second defibrillation electrode, the pace electrode configured to deliver second electrical therapy comprising pacing pulses; and a lead body defining a lumen configured to guide a needle; an inflatable shield disposed at least over a portion of an outer surface of the pace electrode, wherein the inflatable shield is configured to extend laterally away from the pace electrode upon inflation, wherein the inflatable shield is configured to impede an electric field of at least one of the first and second the electrical therapies in a direction away from a heart of the patient; and a septum between the lumen and the inflatable shield, the septum configured to form a seal about the needle, wherein the needle is configured to provide at least one of a gas or a liquid to inflate the inflatable shield.

This summary is intended to provide an overview of the subject matter described in this disclosure. It is not intended to provide an exclusive or exhaustive explanation of the systems, devices, and methods described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

As used herein, relational terms, such as “first” and “second,” “over” and “under,” “front” and “rear,” and the like, may be used solely to distinguish one entity or element from another entity or element without necessarily requiring or implying any physical or logical relationship or order between such entities or elements.

Figure 1A:
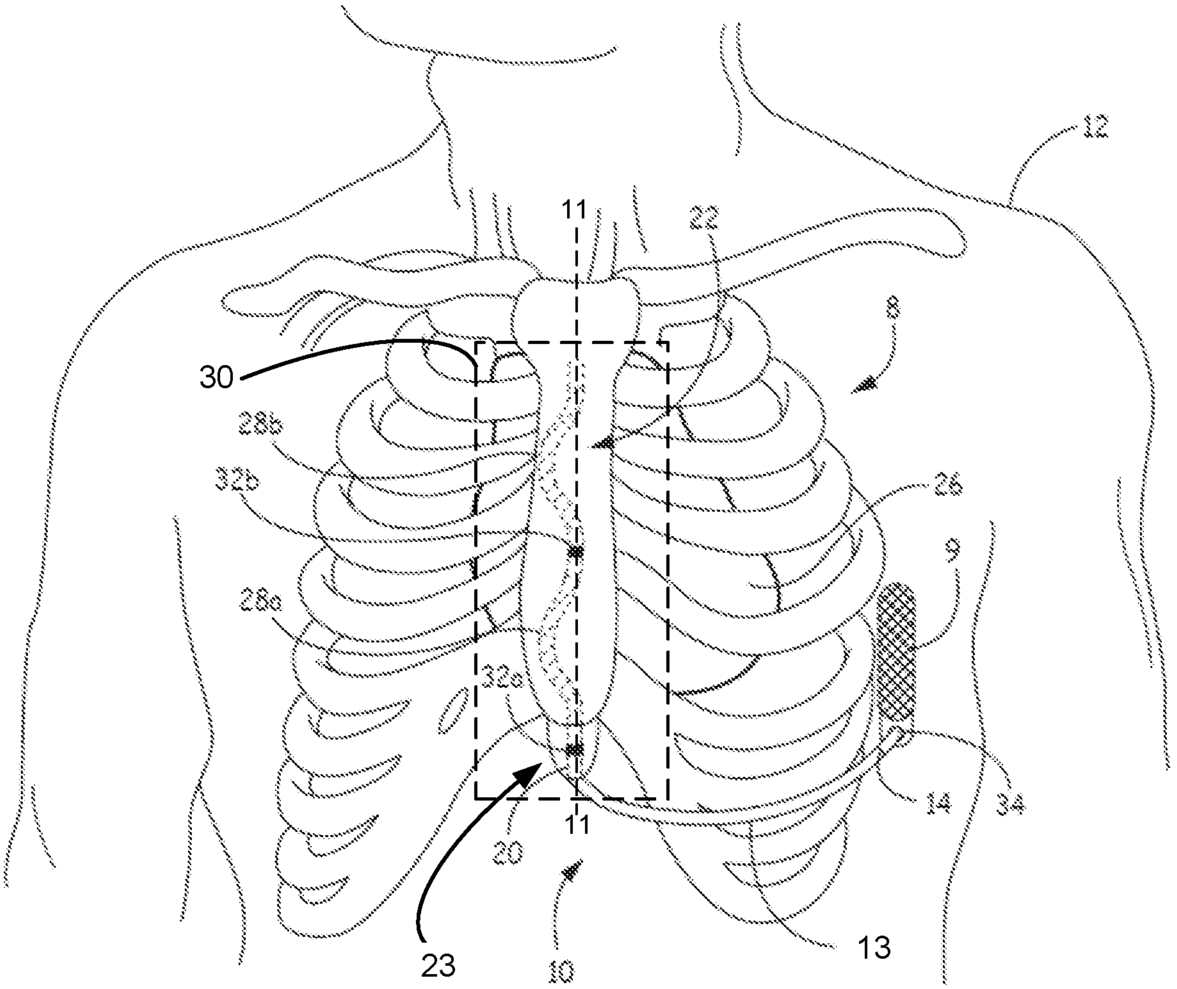
FIG. 1A is a front view of a patient implanted with the extracardiovascular ICD system implanted intra-thoracically.
Figure 1B:
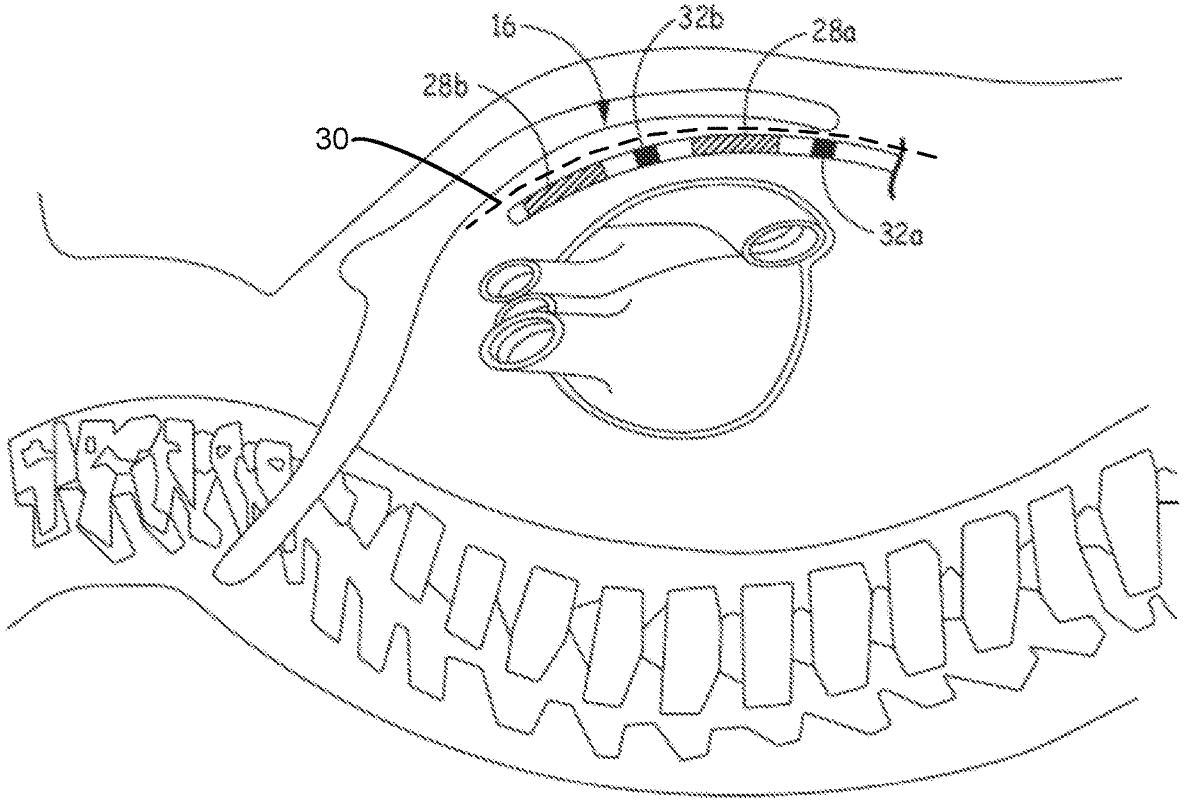
FIG. 1B is a side view of the patient implanted with the extracardiovascular ICD system implanted intra-thoracically.
Figure 1C:
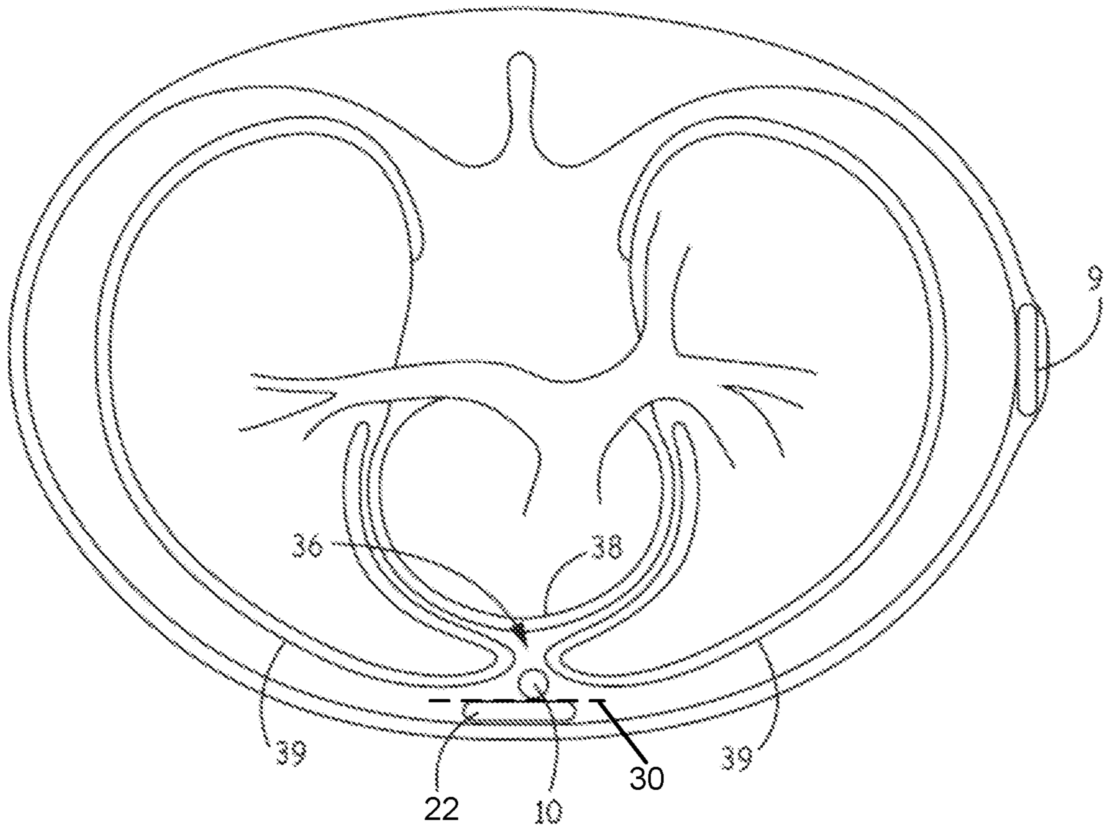
FIG. 1C is a transverse view of the patient implanted with the extracardiovascular ICD system implanted intra-thoracically.

Referring now to the drawings in which like reference designators refer to like elements, there is shown in FIGS. 1A-C conceptual diagrams illustrating various views of an example extracardiovascular implantable cardioverter-defibrillator (ICD) system 8. ICD system 8 includes an ICD 9 connected to an implantable medical lead 10. FIG. 1A is a front view of a patient 12 implanted with extracardiovascular ICD system 8. FIG. 1B is a side view of the patient 12 implanted with extracardiovascular ICD system 8. FIG. 1C is a transverse view of the patient 12 implanted with extracardiovascular ICD system 8.

ICD 9 may include a housing that forms a hermetic seal that protects components of the ICD 9. The housing of ICD 9 may be formed of a conductive material, such as titanium or titanium alloy, which may function as a housing electrode (sometimes referred to as a can electrode). In some embodiments, ICD 9 may be formed to have or may include a plurality of electrodes on the housing. ICD 9 may also include a connector assembly (also referred to as a connector block or header) that includes electrical feedthroughs through which electrical connections are made between conductors of lead 10 and electronic components included within the housing of ICD 9. As will be described in further detail herein, the housing may house one or more processors, memories, transmitters, receivers, sensors, sensing circuitry, therapy circuitry, power sources and other appropriate components. The housing is configured to be implanted in a patient, such patient 12.

ICD 9 is implanted extra-thoracically on the left side of the patient. e.g., under the skin and outside the ribcage (subcutaneously or submuscularly). ICD 9 may, in some instances, be implanted between the left posterior axillary line and the left anterior axillary line of the patient. ICD 9 may, however, be implanted at other extra-thoracic locations on the patient as described later.

Lead 10 may include an elongated lead body 13 having a distal portion 16 sized to be implanted in an extracardiovascular location proximate the heart, e.g., intra-thoracically, as illustrated in FIGS. 1A-C, or extra-thoracically. For example, lead 10 may extend extra-thoracically under the skin and outside the ribcage (e.g., subcutaneously or submuscularly) from ICD 9 toward the center of the torso of the patient, for example, toward the xiphoid process 23 of the patient. At a position proximate xiphoid process 23, the lead body 13 may bend or otherwise turn and extend superiorly. The bend may be pre-formed and/or lead body 13 may be flexible to facilitate bending. In the example illustrated in FIGS. 1A-C, the lead body 13 extends superiorly intra-thoracically underneath the sternum, in a direction substantially parallel to the sternum.

In one example, distal portion 16 of lead 10 may reside in a substernal location such that distal portion 16 of lead 10 extends superior along the posterior side of the sternum substantially within the anterior mediastinum 36. Anterior mediastinum 36 may be viewed as being bounded laterally by pleurae 39, posteriorly by pericardium 38, and anteriorly by the sternum 22. In some instances, the anterior wall of anterior mediastinum 36 may also be formed by the transversus thoracis and one or more costal cartilages. Anterior mediastinum 36 includes a quantity of loose connective tissue (such as areolar tissue), adipose tissue, some lymph vessels, lymph glands, substernal musculature (e.g., transverse thoracic muscle), the thymus gland, branches of the internal thoracic artery, and the ITV.

In another example, lead body 13 may extend superiorly extra-thoracically (instead of intra-thoracically), e.g., either subcutaneously or submuscularly above the ribcage/sternum. Lead 10 may be implanted at other locations, such as over the sternum, offset to the right of the sternum, angled lateral from the proximal or distal end of the sternum, or the like. In other examples, lead 10 may be implanted within an extracardiac vessel within the thorax, such as the ITV, the intercostal veins, the superior epigastric vein, or the azygos, hemiazygos, accessory hemiazygos veins, or between the heart and lung as well as within the pleural cavity. In some examples, distal portion 16 of lead 10 may be oriented differently than is illustrated in FIGS. 1A-1C, such as orthogonal or otherwise transverse to sternum 22 and/or inferior to heart 26. In such examples, distal portion 16 of lead 10 may be at least partially within anterior mediastinum 36.

Lead body 13 may have a generally tubular or cylindrical shape and may define a diameter of approximately 3-9 French (Fr). However, lead bodies of less than 3 Fr and more than 9 Fr may also be utilized. In another configuration, lead body 13 may have a flat, ribbon, or paddle shape with solid, woven filament, or metal mesh structure, along at least a portion of the length of the lead body 13. In such an example, the width across lead body 13 may be between 1-3.5 mm. Other lead body designs may be used without departing from the scope of this application.

Lead body 13 may be formed from a non-conductive material, including silicone, polyurethane, fluoropolymers, mixtures thereof, and other appropriate materials, and shaped to form one or more lumens (not shown), however, the techniques are not limited to such constructions. Distal portion 16 may be fabricated to be biased in a desired configuration, or alternatively, may be manipulated by the user into the desired configuration. For example, the distal portion 16 may be composed of a malleable material such that the user can manipulate the distal portion into a desired configuration where it remains until manipulated to a different configuration.

Lead body 13 may include a proximal end 14 and a distal portion 16 which include electrodes configured to deliver electrical energy to the heart or sense electrical signals of the heart. Distal portion 16 may be anchored to a desired position within the patient, for example, substernally or subcutaneously by, for example, suturing distal portion 16 to the patient's musculature, tissue, or bone at the xiphoid process entry site. In some examples, distal portion 16 may be anchored to the patient or through the use of rigid tines, prongs, barbs, clips, screws, and/or other projecting elements or flanges, disks, pliant tines, flaps, porous structures such as a mesh-like elements and metallic or non-metallic scaffolds that facilitate tissue growth for engagement, bio-adhesive surfaces, and/or any other non-piercing elements.

Lead body 13 may define a substantially linear portion 20 (FIG. 1A) as it curves or bends near the xiphoid process 23 and extends superiorly. As shown in FIG. 1A, at least a part of distal portion 16 may define an undulating configuration distal to the substantially linear portion 20. In particular, distal portion 16 may define an undulating pattern, e.g., zig-zag, meandering, sinusoidal, serpentine, or other pattern, as it extends toward the distal end of lead 10. In other configurations, lead body 13 may not have a substantially linear portion 20 as it extends superiorly, but instead the undulating configuration may begin immediately after the bend.

Distal portion 16 includes one or more defibrillation electrodes configured to deliver an a first electrical therapy, such as anti-tachyarrhythmia shocks, e.g., cardioversion/defibrillation shocks, to heart 26 of patient 12. In some examples, distal portion 16 includes a plurality of defibrillation electrodes spaced a distance apart from each other along the length of distal portion 16. In the example illustrated by FIGS. 1A-I C, distal portion 16 includes two defibrillation electrodes 28*a* and 28*b* (collectively, "defibrillation electrodes 28").

Defibrillation electrodes 28 may be disposed around or within the lead body 13 of the distal portion 16, or alternatively, may be embedded within the wall of the lead body 13. In one configuration, defibrillation electrodes 28 may be coil electrodes formed by a conductor. The conductor may be formed of one or more conductive polymers, ceramics, metal-polymer composites, semiconductors, metals or metal alloys, including but not limited to, one of a combination of the platinum, tantalum, titanium, niobium, zirconium, ruthenium, indium, gold, palladium, iron, zinc, silver, nickel, aluminum, molybdenum, stainless steel. MP35N, carbon, copper, polyaniline, polypyrrole and other polymers. In another configuration, each of defibrillation electrodes 28 may be a flat ribbon electrode, a paddle electrode, a braided or woven electrode, a mesh electrode, a directional electrode, a patch electrode or another type of electrode configured to deliver a cardioversion/defibrillation shock to heart 26 of patient 12.

In one configuration, defibrillation electrodes 28 are spaced approximately 0.25-4.5 cm, and in some instances between 1-3 cm apart from each other. In another configuration, defibrillation electrodes 28 are spaced approximately 0.25-1.5 cm apart from each other. In a further configuration, defibrillation electrodes 28 are spaced approximately 1.5-4.5 cm apart from each other.

In the configuration shown in FIGS. 1A-1C, defibrillation electrodes 28 span a substantial part of distal portion 16. Each of defibrillation electrodes 28 may be between approximately 1-10 cm in length, between approximately 2-6 cm in length, or between approximately 3-5 cm in length. However, lengths of greater than 10 cm and less than 1 cm may be utilized in accordance with the techniques of this disclosure. A total length of defibrillation electrode on distal portion 16, e.g., length of the two defibrillation electrodes 28 combined, may vary depending on a number of variables. In one example, the total length may be between approximately 5-10 cm. However, the defibrillation electrodes 28 may have a total length less than 5 cm and greater than 10 cm in other embodiments. In some instances, defibrillation electrodes 28 may be approximately the same length or, alternatively, different lengths.

Defibrillation electrodes 28 may be electrically connected to one or more conductors, which may be disposed in the body wall of lead body 13 or in one or more insulated lumens (not shown) defined by lead body 13. In an example configuration, each of defibrillation electrodes 28 is connected to a common conductor such that a voltage may be applied simultaneously to all defibrillation electrodes 28 to deliver an anti-tachyarrhythmia shock to heart 26. In other configurations, defibrillation electrodes 28 may be attached to separate conductors such that each defibrillation electrode 28 may apply a voltage independent of the other defibrillation electrodes 28. In this case, ICD 9 or lead 10 may include one or more switches or other mechanisms to electrically connect the defibrillation electrodes together to function as a common polarity electrode such that a voltage may be applied simultaneously to all defibrillation electrodes 28 in addition to being able to independently apply a voltage.

Distal portion 16 may also include one or more pacing and/or sensing electrodes configured to deliver a second electrical therapy, such as pacing pulses to heart 26 and/or sense electrical activity of heart 26. Such electrodes may be referred to as pacing electrodes, sensing electrodes, or pace/sense electrodes. In the example illustrated by FIGS. 1A-1C, distal portion 16 includes two pace/sense electrodes 32*a* and 32*b* (collectively, "pace/sense electrodes 32").

In the illustrated example, pace/sense electrode 32*b* is positioned between defibrillation electrodes 28, e.g., within a gap between the defibrillation electrodes, and pace/sense electrode 32*a* is positioned more proximal along distal portion 16 than proximal defibrillation electrode 28*a*. In some examples, more than one electrode 32 may exist within the gap between defibrillation electrodes 28. In some examples, an electrode 32 is additionally or alternatively located distal of the distalmost defibrillation electrode 28*b*.

In one example, the distance between the closest defibrillation electrode 28 and electrodes 32 is greater than or equal to approximately 2 mm and less than or equal to approximately 1.5 cm. In another example, electrodes 32 may be spaced apart from the closest one of defibrillation electrodes 28 by greater than or equal to 5 mm and less than or equal to 1 cm. In a further example, electrodes 32 may be spaced apart from the closest one of defibrillation electrodes 28 by greater than or equal to 6 mm and less than or equal to 8 mm.

Electrodes 32 may be configured to deliver low-voltage electrical pulses to the heart or may sense a cardiac electrical activity, e.g., depolarization and repolarization of the heart. As such, electrodes 32 may be referred to herein as pace/sense electrodes 32. In one configuration, electrodes 32 are ring electrodes. However, in other configurations electrodes 32 may be any of a number of different types of electrodes, including ring electrodes, short coil electrodes, paddle electrodes, hemispherical electrodes, or directional electrodes. Each of electrodes 32 may be the same or different types of electrodes as others of electrodes 32. Electrodes 32 may be electrically isolated from an adjacent defibrillation electrode 28 by including an electrically insulating layer of material between electrodes 32 and adjacent defibrillation electrodes 28. Each electrode 32 may have its own separate conductor such that a voltage may be applied to or sensed via each electrode independently from another electrode 32.

Electrodes 28 are referred to as defibrillation electrodes, and electrodes 32 are referred to as pace/sense electrodes, because they may have different physical structures enabling different functionality. Defibrillation electrodes 28 may be larger, e.g., have greater surface area, than pace/sense electrodes 32 and, consequently, may be configured to deliver anti-tachyarrhythmia shocks that have relatively higher voltages than pacing pulses. The relatively smaller size of pace/sense electrodes 32 may provide advantages over defibrillation electrodes for delivering pacing pulses and sensing intrinsic cardiac activity, e.g., lower pacing capture thresholds and/or better sensed signal quality. Nevertheless, a defibrillation electrode 28 may be used to deliver pacing pulses and/or sense electrical activity of the heart, such as in combination with a pace/sense electrode 32.

In the configuration shown in FIGS. 1A-1C, each electrode 32 is substantially aligned along a major longitudinal axis 11. In one example, major longitudinal axis 11 is defined by a portion of distal portion 16, e.g., substantially linear portion 20. In another example, major longitudinal axis 11 is defined relative to the body of patient 12, e.g., along the anterior median line (or midsternal line), one of the sternal lines (or lateral sternal lines), left parasternal line, or other line.

In one configuration, the midpoint of each electrode 32*a* and 32*b* is along major longitudinal axis 11 such that each electrode 32*a* and 32*b* is at least disposed at substantially the same horizontal position when the distal portion is implanted within the patient. In some examples, longitudinal axis 11 may correspond to a caudal-cranial axis of the patient and a horizontal axis orthogonal to longitudinal axis 11 may correspond to a medial-lateral axis of the patient. In other configurations, the electrodes 32 may be disposed at any longitudinal or horizontal position along the distal portion 16 disposed between, proximal to, or distal to the defibrillation electrodes 28. In the example illustrated in FIG. 1A, electrodes 32 are disposed along the undulating configuration of distal portion 16 at locations that will be closer to heart 26 of patient 12 than defibrillation electrodes 28 (e.g., at a peak of the undulating configuration that is toward the left side of the sternum). As illustrated in FIG. 1A, for example, electrodes 32 are substantially aligned with one another along the left sternal line. In the example illustrated in FIG. 1A, defibrillation electrodes 28 are disposed along peaks of the undulating configuration that extend toward a right side of the sternum away from the heart. This configuration places pace/sense electrodes 32 at locations closer to the heart than electrodes 28, to facilitate cardiac pacing and sensing at relatively lower amplitudes.

In some examples, pace/sense electrodes 32 and the defibrillation electrodes 28 may be disposed in a common plane when distal portion 16 is implanted extracardiovascularly. In other configurations, the undulating configuration may not be substantially disposed in a common plane. For example, distal portion 16 may define a concavity or a curvature.

Proximal end 14 of lead body 13 may include one or more connectors 34 to electrically couple lead 10 to ICD 9. ICD 9 may also include a connector assembly that includes electrical feedthroughs through which electrical connections are made between the one or more connectors 34 of lead 10 and the electronic components included within the housing. The housing of ICD 9 may house one or more processors, memories, transmitters, receivers, sensors, sensing circuitry, therapy circuitry, power sources (capacitors and batteries), and/or other components. The components of ICD 9 may generate and deliver electrical therapy such as anti-tachycardia pacing, cardioversion or defibrillation shocks, post-shock pacing, and/or bradycardia pacing.

The undulating configuration of distal portion 16 and the inclusion of electrodes 32 between defibrillation electrodes 28 provides a number of therapy vectors for the delivery of electrical therapy to the heart. For example, at least a portion of defibrillation electrodes 28 and one of electrodes 32 may be disposed over the right ventricle, or any chamber of the heart, such that pacing pulses and anti-tachyarrhythmia shocks may be delivered to the heart. The housing of ICD 9 may be charged with or function as a polarity different than the polarity of the one or more defibrillation electrodes 28 and/or electrodes 32 such that electrical energy may be delivered between the housing and the defibrillation electrode 28 and/or electrode 32 to the heart.

Each defibrillation electrode 28 may have the same polarity as every other defibrillation electrode 28 when a voltage is applied to it such that a shock may be delivered from all defibrillation electrodes together. In examples in which defibrillation electrodes 28 are electrically connected to a common conductor within lead body 13, this is the only configuration of defibrillation electrodes 28. However, in other examples, defibrillation electrodes 28 may be coupled to separate conductors within lead body 13 and may therefore each have different polarities such that electrical energy may flow between defibrillation electrodes 28, or between one of defibrillation electrodes 28 and one of pace/sense electrodes 32 or the housing electrode, to provide anti-tachyarrhythmia shock, pacing therapy, and/or to sense cardiac depolarizations. In this case, defibrillation electrodes 28 may still be electrically coupled together, e.g., via one or more switches within ICD 9, to have the same polarity.

In some examples, ICD system 8 may include one or more shields 30. Shield 30 or shields may be configured to be implanted in patient 12 with implantable lead 10 and/or distal portion 16 of lead 10. Shield 30 may be configured to impede an electric field from delivery of an electrical therapy via an electrode, e.g., from a pacing pulse and/or an anti-tachyarrhythmia shock, in a direction from the electrode away from the heart, e.g., in an anterior direction. In this manner, shield 30 may reduce the likelihood that the electrical field will stimulate extracardiac tissue, such as sensory or motor nerves. Furthermore, shield 30 may direct the electrical field toward the heart, allowing lower energy level pacing pulses to capture the heart and/or lower energy level anti-tachyarrhythmia shocks, than may be required without shield 30. Lower energy pacing pulses may also reduce the likelihood that pacing pulses delivered via the pace electrode or defibrillation pulses delivered via defibrillation electrodes 28 stimulate extracardiac tissue, and may result in less consumption of the power source of ICD 9 and, consequently, longer service life for the ICD.

Shield 30 may further be configured to be expanded and/or inflated in a deployed configuration and compressed and/or deflated in an undeployed configuration. In some examples, shield 30 is configured to be accommodated by an introducer configured to deliver lead 10 and shield 30, e.g., in the undeployed configuration, while still providing a relatively larger shielding area in the deployed configuration. In some examples, shield 30 may have an asymmetric shape configured to improve insertion and withdrawal of lead 10 including shield 30, e.g., insertion and removal via an introducer. It should be understood that various aspects of the techniques of this disclosure may be applied to implantable systems other than ICD 9, including, but not limited to, bradycardia pacemaker systems. For example, a lead that does not include defibrillation electrodes 28 may include one or more shields 30 and may be used with a pacemaker system without defibrillation capabilities.

Figure 2A:
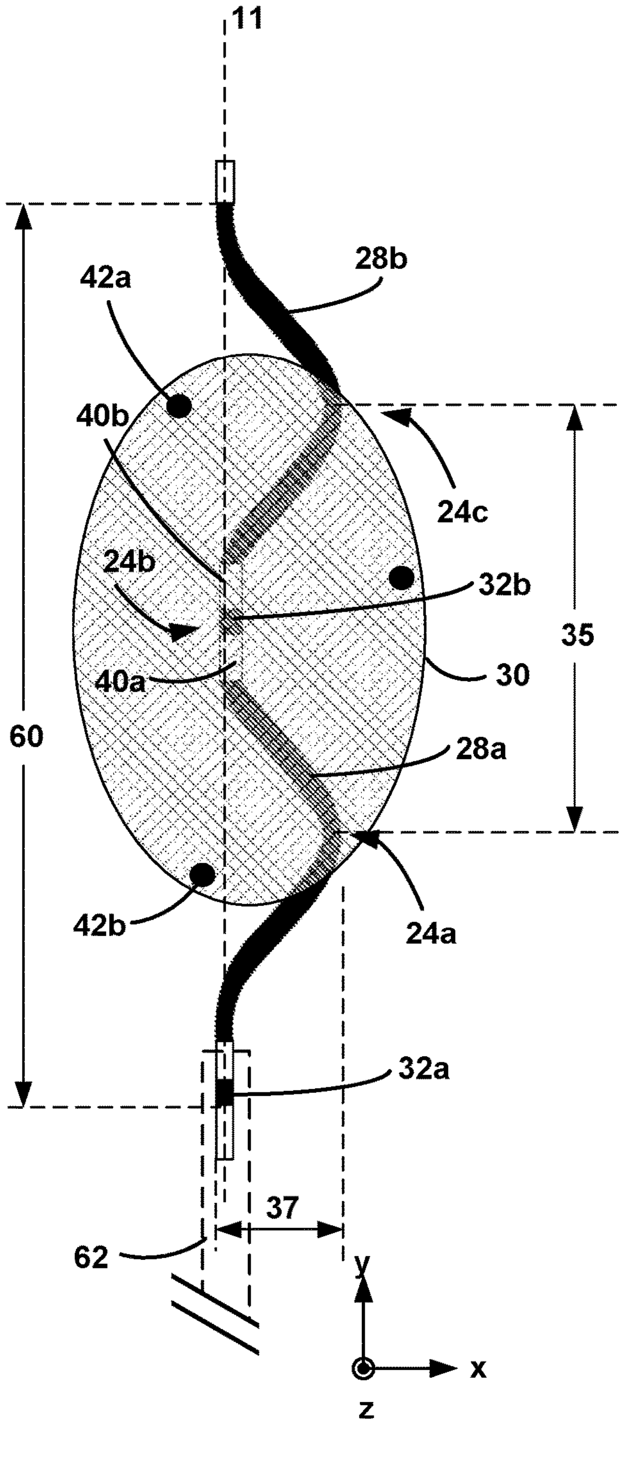
FIG. 2A is a conceptual diagram illustrating an anterior view of a distal portion of an example implantable medical lead and an example shield in a deployed configuration.
Figure 2B:
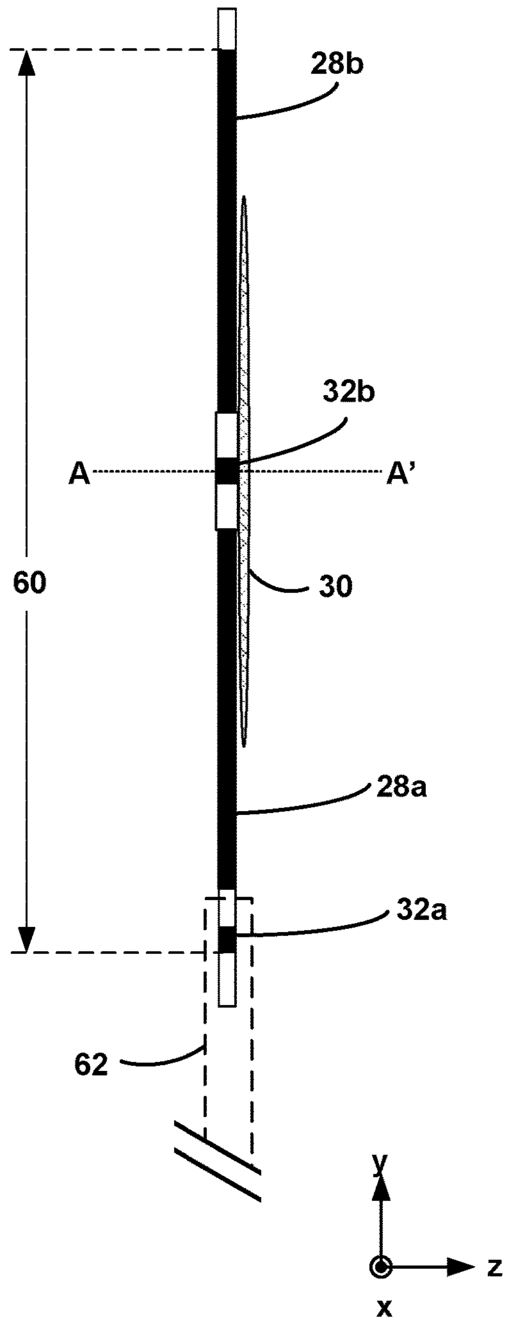
FIG. 2B is a conceptual diagram illustrating a lateral view of the distal portion of the example implantable medical lead and shield in the deployed configuration of FIG. 2A.
Figure 3A:
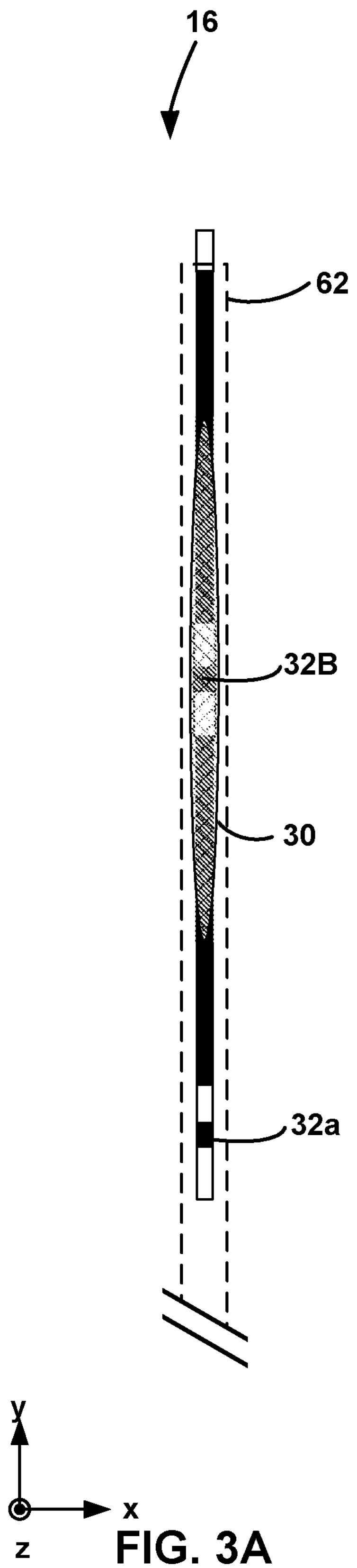
FIG. 3A is a conceptual diagram illustrating an anterior view of the distal portion of the example implantable medical lead and example shield of FIG. 2A in an undeployed configuration.
Figure 3B:
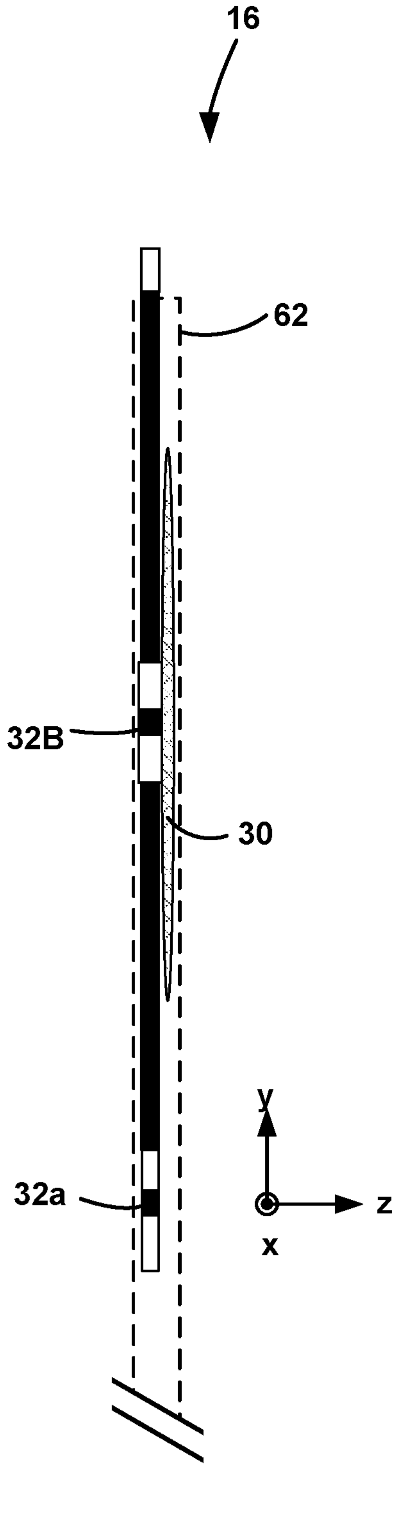
FIG. 3B is a conceptual diagram illustrating a lateral view of the distal portion of the example implantable medical lead and shield in the undeployed configuration of FIG. 3A.

FIGS. 2A-2B and 3A-3B are conceptual diagrams illustrating views of example shield 30 and distal portion 16 of implantable medical lead 10. In particular, FIG. 2A is a conceptual diagram illustrating an anterior, or “top,” view of a distal portion 16 of an example implantable medical lead 10 and an example shield 30 in a deployed configuration, and FIG. 3A is a conceptual diagram illustrating an anterior view of distal portion 16 of the example implantable medical lead 10 and example shield 30 of FIG. 2A but in an undeployed configuration. FIG. 2B is a conceptual diagram illustrating a lateral, or “side” view of the distal portion 16 of the example implantable medical lead 10 and example shield 30 in the deployed configuration of FIG. 2A, and FIG. 3B is a conceptual diagram illustrating a lateral view of the distal portion 16 of the example implantable medical lead 10 and example shield 30 in the undeployed configuration of FIG. 3A. FIGS. 2A-2B and 3A-3B are described concurrently below.

As illustrated in FIG. 2A, the undulating configuration of distal portion 16 in the deployed configuration may include a plurality of peaks along the length of the distal portion. In the example illustrated by FIG. 2A, distal portion includes three peaks 24*a*, 24*b*, and 24*c* (collectively. “peaks 24”). Other configurations, however, may include any number of peaks 24. In the examples shown, a portion of distal portion 16 is illustrated as being overlapped by shield 30. In some examples, all of distal portion 16 is illustrated as being overlapped by shield 30 (not shown), e.g., extending at least as long as length 60 along longitudinal axis 11. In the examples shown in FIGS. 2A-3B, shield 30 is positioned anterior to distal portion 16 relative to patient 12.

The example undulating configuration of distal portion 16 shown in FIG. 2A may define a peak-to-peak distance 35, which may be variable or constant along the length of distal portion 16. In the configuration illustrated in FIG. 2A, the undulating configuration defines a substantially sinusoidal configuration, with a constant peak-to-peak distance 35 of approximately 2.0-5.0 cm. The undulating configuration may also define a peak-to-peak width 37, which may also be variable or constant along the length of the undulating configuration. In the configuration illustrated in FIG. 2A, the undulating configuration defines a substantially sinusoidal shape, with a constant peak-to-peak width 37 of approximately 0.5-2.0 cm. However, in other instances, the undulating configuration may define other shapes and/or patterns, e.g., S-shapes, wave shapes, or the like.

Defibrillation electrodes 28 may extend along, e.g., be disposed on or cover, a substantial part of the undulating configuration of distal portion 16, e.g., along at least 80% of the undulating portion. Defibrillation electrodes 28 may extend along more or less than 80% of the undulating configuration. As another example, defibrillation electrodes 28 may extend along at least 90% of the undulating configuration.

Defibrillation electrode 28*a* extends along a substantial portion of the undulating configuration of distal portion 16 from the proximal end to peak 24*b*, e.g., along a substantial portion of the first “wave” associated with peak 24*a*, and the defibrillation electrode segment 28*b* extends along a substantial portion of the undulating configuration from peak 24*b* to the distal end of the undulating configuration, e.g., along a substantial portion of the second “wave” associated with peak 24*c*). In the example illustrated in FIG. 2A, a part of the undulating configuration on which defibrillation electrodes 28 are not disposed is a gap between defibrillation electrodes 28*a* and 28*b*, on peak 24*b*, where electrode 32*b* is disposed.

As illustrated in FIGS. 2A and 2B, distal portion 16 of lead 10 may include lead body portion 40*a* and lead body portion 40*b* (collectively. “lead body portions 40”). Lead body portions 40 extend between pace/sense electrode 32*b* and a respective one of defibrillation electrodes 28. Lead body portions 40 may provide a relatively even or smooth surface transition between the outer profile of pace/sense electrode 32*b* and the outer profiles of defibrillation electrodes 28. Conductors coupled to electrodes 32*b* and 28*b* may extend through lead body portion 40*a*, and a conductor coupled to electrode 28*b* may extend through lead body portion 40*b*. Lead body portions 40*a* and 40*b* may formed of one or more polymers, which may be the same as or different from shields 30 and 31, and/or other portions of lead body 13.

As illustrated by FIGS. 2A-3B, distal portion 16 of lead 10 may comprise a shield 30. In the illustrated examples, shield 30 is positioned on peak 24*b* of the undulating configuration of distal portion 16. In some examples, shield 30 may be positioned anywhere along distal portion 16, e.g., so as to "cover" or be anterior to at least a portion of one or more of pace/sense electrodes 32 or defibrillation electrodes 28. In the examples shown, shield 30 covers or is otherwise disposed over a portion of an outer surface of pace/sense electrode 32*b*. Shield 30 does not cover an entirety of the outer surface of pace/sense electrode 32*b*, e.g., circumferentially around pace/sense electrode 32*b*.

In the examples shown, shield 30 has a substantially elliptical shape. In the example shown in FIG. 2A, shield 30 has an elliptical shape with two axes of symmetry, a major axis in the direction of longitudinal axis 11 (e.g., the y-direction), and a minor axis along the width direction (e.g., the x-direction). For example, the longitudinal axis of shield 30 is along length 60 of distal portion 16 of implantable medical lead 10. In the example shown, shield 30 extends along at least a portion of defibrillation electrodes 28. In other examples, shield 30 extends along at least the entire length 60 and width 37 of distal portion 16 in the deployed configuration, e.g., covering defibrillation electrodes 28 and pace/sense electrodes 32. In some examples, shield 30 may have its major axis substantially aligned with the longitudinal axis of distal portion 16.

In the examples shown, shield 30 is asymmetric along any other axis. In some examples, shield 30 may be asymmetric about the longitudinal and/or width axes relative to distal portion 16 and longitudinal axis 11, e.g., shield 30 may be "rotated" about the z-axis relative distal portion 16 and have its major and minor axes along directions other than longitudinal axis 11. For example, shield 30 may be rotated to provide better shielding relative to patient anatomy when distal portion 16 is in the deployed configuration. In some examples, shield 30 may be rotated to provide better mechanical compatibility with the undulating shape of distal portion 16, e.g., to relieve tension via shield attachment points to distal portion 16 causing distal portion 16 to compress, expand, or twist due to an elastic or shape memory property of shield 30 allowing shield 30 to expand upon deployment. In some examples, shield 30 may be rotated to provide a greater attachment area to distal portion 16. In some examples, shield 30 may rotated or not and/or shifted (e.g., in the x-direction and/or the y-direction) or not for the same reasons as described above, e.g., to provide improved shielding relative to patient anatomy, an improved mechanical compatibility with distal portion 16, and/or an improved attachment area to distal portion 16. In some examples, shield 30 may have any other suitable shape. In some examples, shield 30 has a generally asymmetric shape with a longitudinal axis corresponding to a direction of the maximum extent and/or length of shield 30.

Shield 30 may be electrically insulative and biocompatible. In some examples, shield 30 comprises a polymer, such as polyurethane. In some examples, shield 30 is configured to be folded or wrapped around pace/sense electrode 32*b* for delivery via a lumen of an implant tool, and configured to elastically unfold or unwrap to a relaxed condition, e.g., such as the deployed configuration shown in FIG. 2A, when released from the lumen. In some examples, shield 30 comprises elastic or super-elastic polymer or metallic structures, e.g., Nitinol structures, to encourage the deployment of shield 30, support articulation of shield 30, and/or support shield 30 in the deployed, relaxed configuration. The deployed and/or articulated configuration may be substantially planar, as illustrated in FIG. 2, or may be non-planar. For example, portions of shield 30 spaced further away laterally from pace/sense electrode 32*b* may be situated more posteriorly than portions closer to the electrode, e.g., in the shape of a cup or bowl. In some examples, shield 30 may be a substantially solid material, and in other examples shield 30 may have structure in at least portions of it area and/or volume, e.g., at least a portion of shield 30 may be a membrane web.

Such support structures may be partially or fully embedded within a primary material of shield 30, or attached to one or more outer surfaces of shield 30. In some examples, a support structure is located circumferentially around a perimeter of shield 30, e.g., spaced a greatest distance laterally from the shield. However, other support structure locations are possible. For example, one or more support structures may extend in radial or lateral direction from the electrode, e.g., from near electrode to near a periphery of the shield.

In some examples, shield 30 may be a single layer of a material, and may be substantially flat or planar as mentioned above. For example, as illustrated in FIG. 2B, shield 30 extends substantially within the x-y plane having a thickness in the z-direction and does not curve and/or bend in the positive or negative z-direction, and the thickness of shield 30 may be substantially constant throughout its area. In other examples, shield 30 may have a curve and/or bend, or may be concave and/or convex relative to the z-direction, or may have thickness variation throughout its area.

In some examples, shield 30 may be inflatable, such as a balloon. Inflatable shield 30 may be configured to inflate with at least one of a gas or a liquid. For example, inflatable shield 30 may be configured to inflate with sterile water, sterile saline, a saline-contrast mixture, or the like. In some examples, at least one of lead 10 and distal portion 16 include a lumen configured to be coupled with inflatable shield 30, and the lumen may be configured to provide gas or liquid to and from inflatable shield 30.

In some examples, inflatable shield 30 may be a single layer of material, or multiple layers of material, for example, two or more layers of polyurethane. For example, shield 30 may comprise a first layer of polyurethane cast along at least a portion of length 60, and in some examples, the entire length 60. The cast may bond the first layer to at least a portion of defibrillation electrodes 28 and may bond the defibrillation electrodes 28 in place. Inflatable shield 30 may include a hole or aperture proximal of pacing/sense electrode 32*b*, e.g., to vent inflatable shield 30 on the anterior side of inflatable shield 30. Shield 30 may comprise a second precast layer of polyurethane to cover a desired area and the edges of the second layer may be bonded to the first layer and/or distal portion 16, e.g., via an adhesive, a thermal bond, or any suitable bonding material or technique.

In some examples, inflatable shield 30 may be configured to receive an inflation medium from an inflation needle, e.g., via the hole/aperture, the needle inserted into a lumen of lead 10, e.g., near the distal end of a connector grip sleeve. In some examples, inflatable shield 30 may be configured to be inflated via a small inflation tube. In other examples, inflatable shield 30 may be inflatable via an inflation needle inserted directly into a connector at proximal end 14 of lead body 13, such as a DF4 connector. In some examples, proximal end 14 of lead body 13 may include a termination and/or connector fluidically coupled with a lumen, e.g., an inflation lumen, through lead body 13 that is also fluidically coupled with inflatable shield 30.

In some examples, an inflation needle may not be needed. For example, a proximal end of an inflation lumen of lead body 13 may be configured to receive, or be received within, a tube via a friction fit. In some examples, a cap may be used to fluidically seal, or to improve or ensure a fluidic seal between the tube and the lumen at the proximal end of lead body 13, and the tube maybe connected to a fluid source configured to provide a fluid to inflate inflatable shield 30.

In some examples, inflatable shield 30 may be configured to be implanted and/or delivered via a relatively small introducer, e.g., 36 Fr or less, or 20 Fr or less, or 18 Fr or less, or 14 Fr or less, or 12 Fr or less, or any suitable size introducer. For example, inflatable shield 30 may comprise a balloon wall thickness such that inflatable shield 30 may be implanted and/or delivered via a 14 Fr introducer.

In the examples shown in FIGS. 2A and 2B, shield 30 (non-inflatable shield 30 or inflatable shield 30) and distal portion 16 are in the deployed configuration. For example, shield 30 and distal portion 16 as illustrated in FIGS. 2A and 2B have been introduced via introducer 62. For example, distal portion 16 including shield 30 may be positioned at a delivery site with a lumen of introducer 62, and introducer 62 may be drawn back from distal portion 16 causing distal portion 16 to exit the lumen, or distal portion 16 may be pushed out of the lumen. Upon exiting the lumen distal portion 16 and shield 30 may be configured to self-deploy to the deployed configuration, e.g., the size and shape illustrated and described above at FIGS. 2A and 2B. For example, distal portion 16 and shield 30 may be elastic and compressed within the lumen of introducer 62, and may self-deploy to their relaxed-state shape when released from the lumen. In some examples, distal portion 16 and/or shield 30 may have shape memory and may self-deploy to their designed shapes upon release from introducer 62.

FIGS. 3A and 3B illustrate distal portion 16 and shield 30 compressed to a first shape for implantation of lead 10, e.g., in an undeployed configuration. For example, the undulating shape of distal portion 16 may be substantially straight and in the first shape, e.g., with electrodes 28 and 32 are configured to be aligned substantially along a common axis when shield 30 is compressed, unexpanded, deflated, or uninflated, and or undeployed. In the example shown, distal portion 16 and shield 30 in the undeployed configuration are within the lumen of introducer 62, and shield 30 may be compressed and/or wrapped about distal portion 16 in the first shape in the undeployed configuration within introducer 62. Upon deployment, distal portion 16 may be configured to elastically expand to its undulating shape, and shield 30 may be configured to elastically expand to its second shape, which may be asymmetric, kidney bean shaped, elliptical, or any other suitable shape. Upon removal, distal portion 16 and shield 30 may be configured to compress, deflate, or the like, to the first shape.

In the deployed configuration, shield 30 expanded to the asymmetric shape is greater than a length of pace electrode 32*b*, and the width of shield 30 expanded to the asymmetric shape is greater than a width of pace electrode 32*b*. In some examples, shield 30 in the expanded, deployed configuration is configured to extend at least 10 millimeters from pace electrode 32*b* in any lateral direction. In some examples, the length of shield 30 expanded to an asymmetric shape in the deployed configuration is greater than length 60 of distal portion 16 and the width of shield 30 expanded to the asymmetric shape is greater than width 37 of distal portion 16. In some examples, shield 30 is configured to contract into introducer 62, e.g., during removal of distal portion 16 and lead 10. For example, distal portion 16 may be configured to contract and/or compress into introducer 62 and introducer 62 is advanced along distal portion 16 or distal portion 16 is retracted into the lumen of introducer 62. Shield 30 may be configured to contract and/or compress along with distal portion 16, e.g., from its second shape in the deployed configuration to its first shape in the undeployed configuration.

Figure 4:
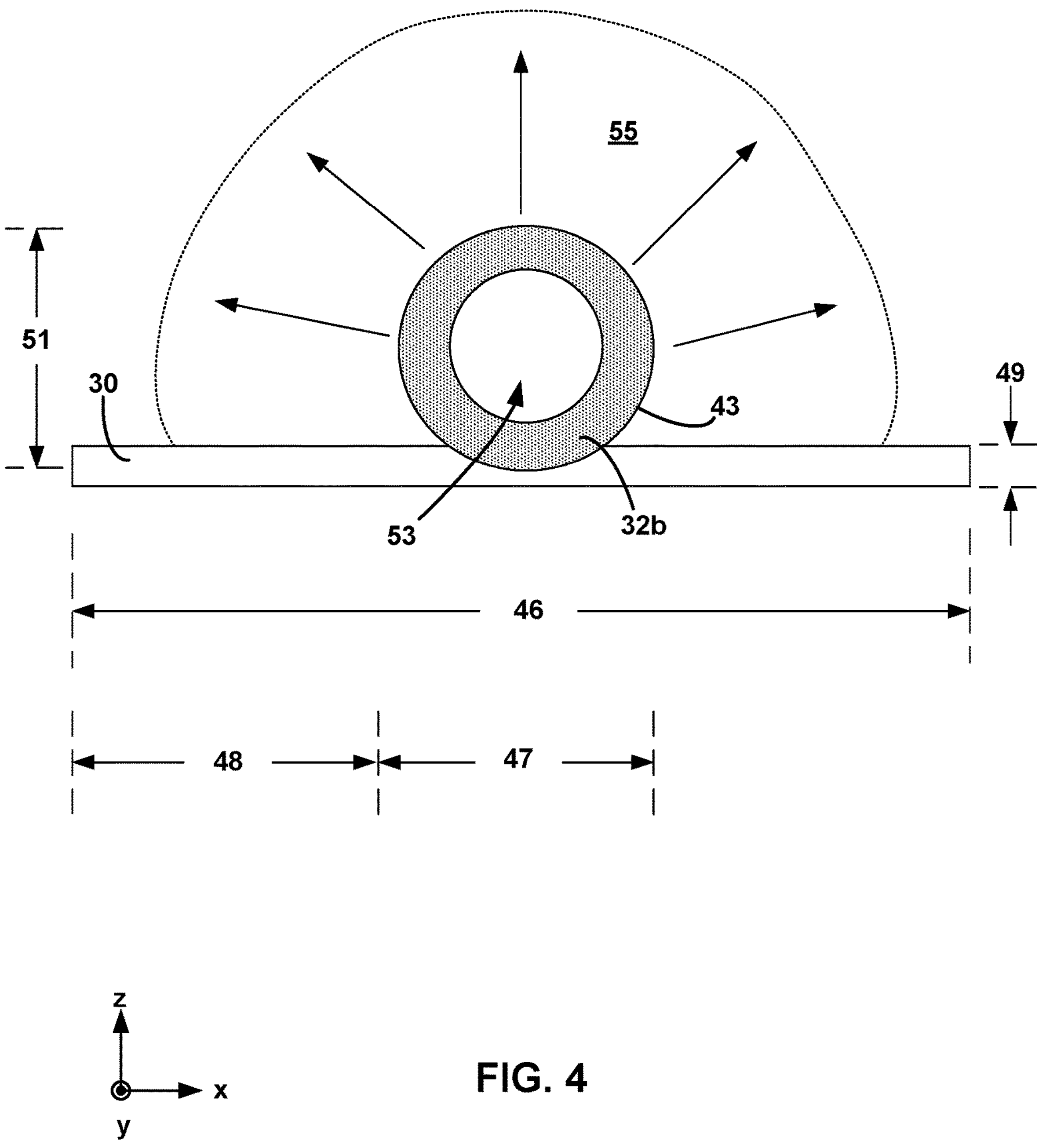
FIG. 4 is a conceptual, cross-sectional view of an electrode of an example implantable medical lead and an example shield.

FIG. 4 is a conceptual, cross-sectional view of electrode 32*b* of an example implantable medical lead 10 and shield 30. FIG. 4 is a cross-sectional view taken at line A-A' in FIG. 2B. As illustrated in FIG. 4, pace/sense electrode 32*b* may define a lumen 53, e.g., may be in the form of a ring, and a conductor coupled to electrode 28*b* may extend through lumen 53. Although illustrated in FIG. 4 as a ring, pace/sense electrodes 32 may have other shapes, including partial or segmented ring shapes or arc shapes, in which one or more electrodes or electrode segments extend less than 360-degrees around a circumference of the lead.

Since shield 30 only covers an anterior portion of outer surface of one or more of electrodes 28 and/or 32 (e.g., surface 43 of pace/sense electrode 32*b* in the example shown), a depth 49 of a shield 30 may be less than a depth of electrodes 28 and/or 32 (e.g., depth 51 of pace/sense electrode 32*b* in the example shown), such as less than one half of the depth of any of electrodes 28 and/or 32. Although illustrated as substantially constant, depth 49 of shield 30 may vary. For example, depth 49 may increase toward electrodes 28 and/or 32, and/or decrease toward an edge of shield 30, e.g., to provide a smooth or otherwise desired transition between shield 30 and electrodes 28 and/or 32, and/or between shield 30 and tissue of the patient. Additionally, although defibrillation electrodes 28, pace/sense electrodes 32, and lead body portions 40*a* and 40*b* are shown in FIG. 2B as having substantially equal depths (e.g., circumferences) that are greater than depth 49 of shield 30, in other examples depth 49 of shield 30 may be similar to that of lead body portions 40*a* and 40*b* and pace/sense electrode 32*b* may extend outward from lead body portions 40*a* and 40*b* and shield 30, e.g., due to having a greater depth or being offset from a longitudinal axis defined by lead body portions 40*a* and 40*b*. In some examples, depth 49 of shield 30 may be greater than a depth of electrodes 28 and/or 32, e.g., such as with an inflatable shield 30.

As illustrated in FIG. 4, pacing pulses delivered by ICD 9 via pace/sense electrode 32*b* result in an electrical field 55 proximate the electrode, that "spreads" from electrode outer surface 43. Similarly, although not shown, anti-tachyarrhythmia shocks delivered by ICD 9 via defibrillation electrodes 28 result in an electric field proximate the electrode that spreads from the electrode outer surface similar to that shown for pace/sense electrode 32*b*. Shield 30 may reduce and/or impede the electrical field in directions from the electrode toward the shield, and allows the spread in directions from the electrode away from shield 30. In this manner, shield 30 may be configured to make any or all of pace/sense electrodes 32 and defibrillation electrodes 28 directional.

As illustrated in FIG. 2A, shield 30 may extend laterally away from pace/sense electrode 32*b* in the deployed configuration, e.g., in a substantially planar manner, such that the dimensions of shield 30 in a plane are greater than those of pace/sense electrode 32*b* in the plane. In this manner, shield 30 may further (or more effectively) limit the directions, e.g., radial angles, of the spread of the electrical field generated by the pacing pulse from pace/sense electrode 32*b*. The plane in which shield 30 extends laterally from pace/sense electrode 32*b* may be the same plane in which peaks 24 of the undulating configuration extend, or a substantially parallel plane.

The portion of the outer surface of pace/sense electrode 32*b* over which shield 30 is positioned may be referred to as an "anterior portion" of the outer surface of pace/sense electrode 32*b*, since that portion of pace/sense electrode 32*b* may be more anteriorly positioned within the patient when distal portion 16 of lead 10 is implanted within patient. With shield 30 positioned over an anterior portion of the outer surface of pace/sense electrode 32*b*, shield 30 may be positioned anteriorly relative to the central longitudinal axis 11 of pace/sense electrode 32*b*. With shield 30 positioned over an anterior portion of the outer surface of pace/sense electrode 32*b*, and distal portion 16 implanted within the patient as illustrated in FIGS. 1A-1C, shield 30 may impede the electrical field in directions away from heart 26, referred to as anterior directions.

In some examples, shield 30 includes a plurality of radiopaque markers, including radiopaque marker 42*a* and radiopaque marker 42*b* (collectively, "radiopaque markers 42"). Shield 30 may include any number of radiopaque markers or no radiopaque markers. Radiopaque markers 42 may be distributed symmetrically or asymmetrically on shield 30, e.g., relative to pace/sense electrode 32*b*. Radiopaque markers 42 may be positioned on shield 30 to allow a user to visualize at least one of a position or an orientation of the shield within the patient by identification of the radiopaque markers in a fluoroscopic or other image. Radiopaque markers 42 may be different from each other in one or more ways, e.g., size, shape, or orientation, to allow, for example, a physician to differentiate between radiopaque markers 42, in this way facilitating visualization of the orientation of shield 30. For example, one of radiopaque markers 42 positioned on shield 30 may be larger than the rest such that the physician may determine, based on the position of the larger radiopaque marker (e.g., relative to the rest of radiopaque markers 42), the orientation of shield 30.

Figure 5A:
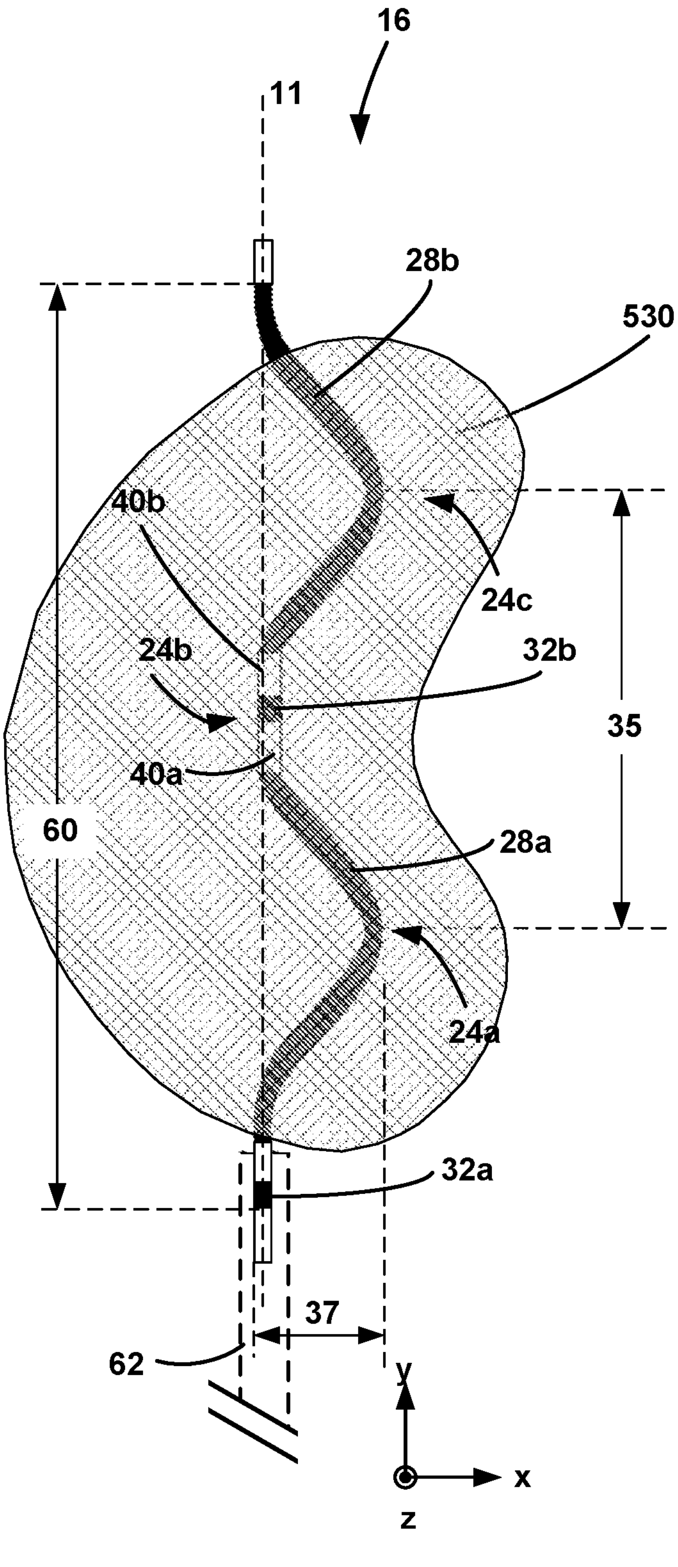
FIG. 5A is a conceptual diagram illustrating an anterior view of a distal portion of another example implantable medical lead and another example shield in a deployed configuration.

FIG. 5A is a conceptual diagram illustrating an anterior view of a distal portion 16 of another example implantable medical lead 10 and another example shield 530 in a deployed configuration. Lead 10 and distal portion 16 may be as described above at FIGS. 2-4. Shield 530 may be substantially similar to shield 30 described above but having a different shape.

In the example shown, shield 30 has a "kidney bean" shape, which may be generally asymmetric. In some examples, shield 530 may have one axis of symmetry, e.g., along the x-direction as shown, or no axis of symmetry. In some examples, shield 530 may have a shape substantially similar to the elliptical shape of shield 30 but having an indent at one side of the elliptical shape.

In some examples, shield 530 may be configured to improve deployment and removal of lead 10, such as by improving deployment and removal of distal portion 16 and shield 530. For example, the indent shape of shield 530 may generally follow the shape of distal portion 16 between peaks 24*a* and 24*c*. The shape, and optionally atraumatic edges, of shield 530 may improve retraction of distal portion 16 and shield 530 into introducer 62 by reducing excess shield material and rough edges than may catch and/or "hang up" on introducer 62, such as at the edges of the distal end lumen opening of introducer 62. In some examples, the kidney bean shape of shield 530 may relieve stresses between distal portion 16 and shield 530 bonded and/or attached along at least a portion of the length of distal portion 16. In some examples, the kidney bean shape of shield 530 may be configured to improve blocking of electrical signals in the anterior direction for portions of the anatomy of patient 12.

Figure 5B:
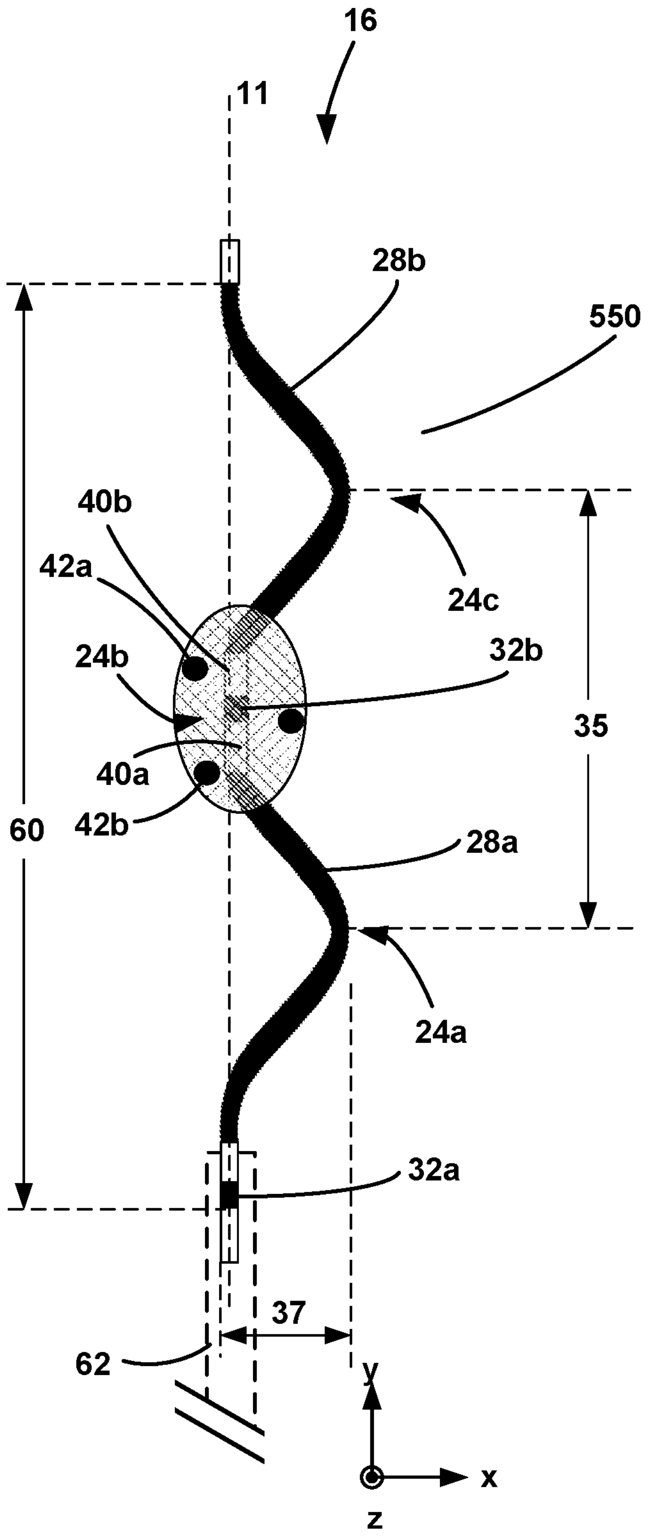
FIG. 5B is a conceptual diagram illustrating an anterior view of a distal portion of another example implantable medical lead and another example shield in a deployed configuration.

FIG. 5B is a conceptual diagram illustrating an anterior view of a distal portion 516 of another example implantable medical lead 10 and another example shield 550 in a deployed configuration. Lead 10 and distal portion 16 may be as described above at FIGS. 2-4. Shield 530 may be substantially similar to shield 30 described above but having a different shape.

In the example shown, shield 550 have a reduced width and length relative to shield 30. For example, shield 550, in the deployed configuration, may be configured to extend to shield pace/sense electrode 32*b* and a portion of defibrillation electrodes 28*a* and 28*b* adjacent to lead body portions 40*a* and 40*b*. For example, shield 550 may extend to shield 90% or less of defibrillation electrodes 28*a* and 28*b*, or 50% or less of defibrillation electrodes 28*a* and 28*b*, or 10% or less of defibrillation electrodes 28*a* and 28*b*.

In some examples, shield 550 may be configured to improve deployment and removal of lead 10, such as by improving deployment and removal of distal portion 16 and shield 550 via a reduced size relative to shield 30 for example, while still shielding pace/sense electrode 32*b* and edge effects resultant from defibrillation electrodes 28*a* and 28*b*, e.g., at the edges of defibrillation electrodes 28*a* and 28*b* adjacent to lead body portions 40*a* and 40*b*. The shape, and optionally atraumatic edges, of shield 550 may improve retraction of distal portion 16 and shield 550 into introducer 62 by reducing excess shield material and rough edges than may catch and/or "hang up" on introducer 62, such as at the edges of the distal end lumen opening of introducer 62. In some examples, shield 550 may be configured to improve blocking of electrical signals in the anterior direction for portions of the anatomy of patient 12.

Figure 6:
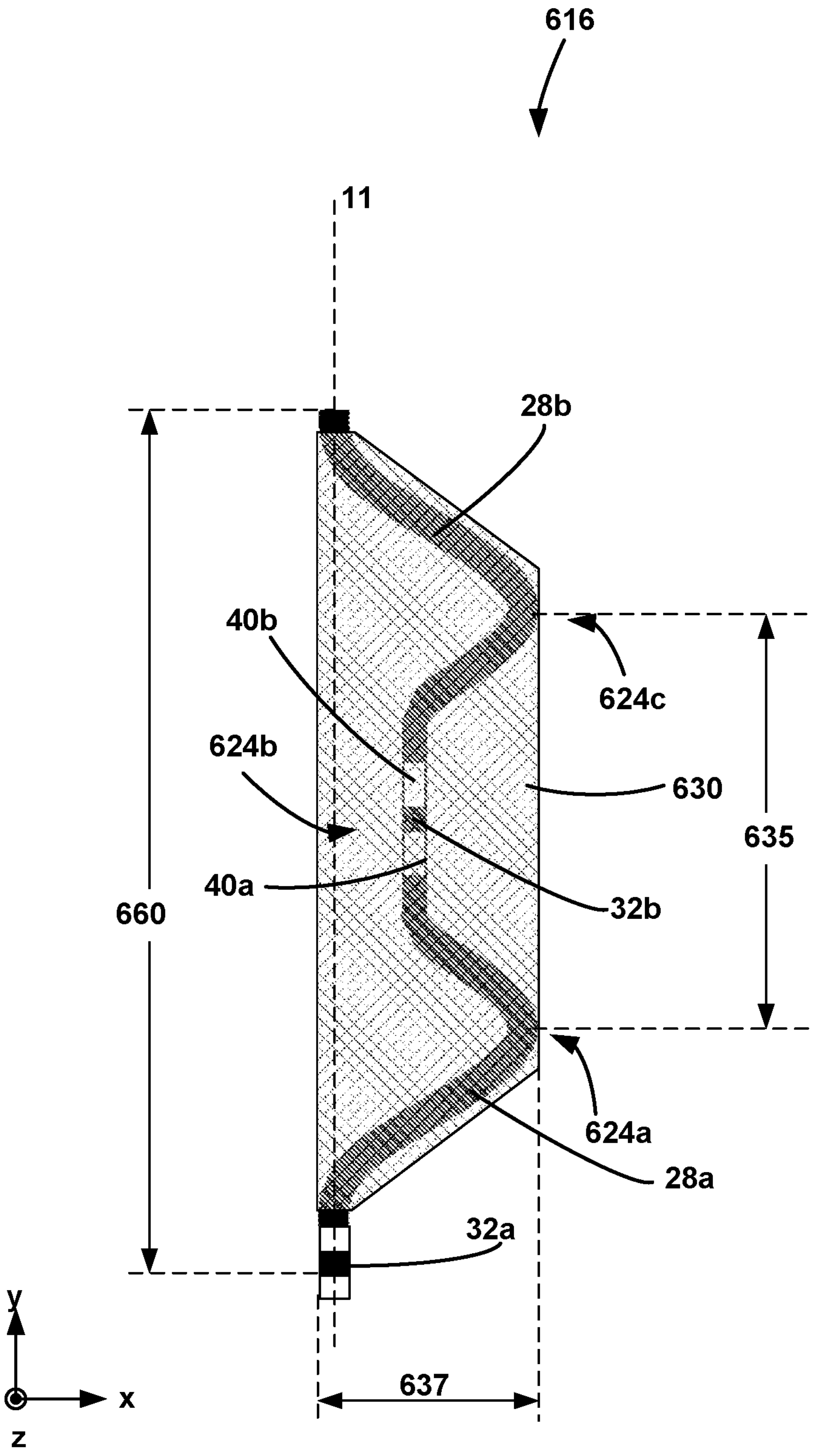
FIG. 6 is a conceptual diagram illustrating an anterior view of a distal portion of another example implantable medical lead and another example shield in a deployed configuration.

FIG. 6 is a conceptual diagram illustrating an anterior view of another example distal portion 616 of example implantable medical lead 10 and another example shield 630 in a deployed configuration. Lead 10 and distal portion 616 may be substantially similar to lead 10 and distal portion 16 described above at FIGS. 2-4, but with a reshaped distal portion 616. Shield 630 may be substantially similar to any of shields 30 and/or 530 described above but having a different shape.

In the example shown, distal portion 616 has a different undulating shape relative to distal portion 16. For example, peak 624*b* is shifted in the x-direction towards peaks 624*a* and 624*c* from longitudinal axis 11. In some examples, distal portion 616 may have a length 660, which may the same or longer or shorter than length 60 of distal portion 16 of FIG. 5A. Distal portion 616 may have a peak to peak length 635 that is the same or longer or shorter than length 35 of distal portion 16 of FIG. 5A, and distal portion 616 may have a width 637 that is the same or longer or shorter than width 37 of distal portion 16 of FIG. 5A.

In some examples, shield 630 may be attached and/or bonded along its entire length to distal portion 16. e.g., following the undulating shape of distal portion 16. The shape of distal portion 616 may enable or improve bonding of shield 630 to distal portion 616 along its entire length 660, e.g., along the undulating shape of at least a portion, or substantially all, of electrodes 28 and 32 and lead body portions 40*a* and 40*b*. In some examples, shield 630 may be a thin, stretchable, elastic membrane configured to return to its original shape (as shown) in the deployed configuration. In some examples, shield 630 is configured to improve lead stability and ensure its deployment via bonding to at least both defibrillation electrodes 28*a* and 28*b*.

In some examples, shield 630 is configured to reduce or prevent in-growth of tissue between shield 630 and distal portion 616, e.g., via bonding along the entire length of distal portion 616 and/or shield 630. Shield 630 may be configured to be release from tissue when being removed, e.g., via bonding preventing in-growth between shield 630 and distal portion 616, or via any other means of releasing from tissue such as a coating. e.g., a hydrophobic and/or oleophobic coating, or via a stretch-release mechanism configured to decouple or debond shield 630 from surrounding tissue by virtue of shield 630 stretching and/or compressing. In some examples, shield 630 is tapered and bonded at one or both of the distal and proximal ends of distal portion 616. In some examples, tapering and bonding shield 630 at one or both of the distal and proximal ends of distal portion 616 may improve deployment and/or removal of distal portion 616 and shield 630 and may reduce catching and/or hang-up of distal portion 616 and shield 630 on introducer 62 and/or introducer valves during deployment and/or removal.

Figure 7:
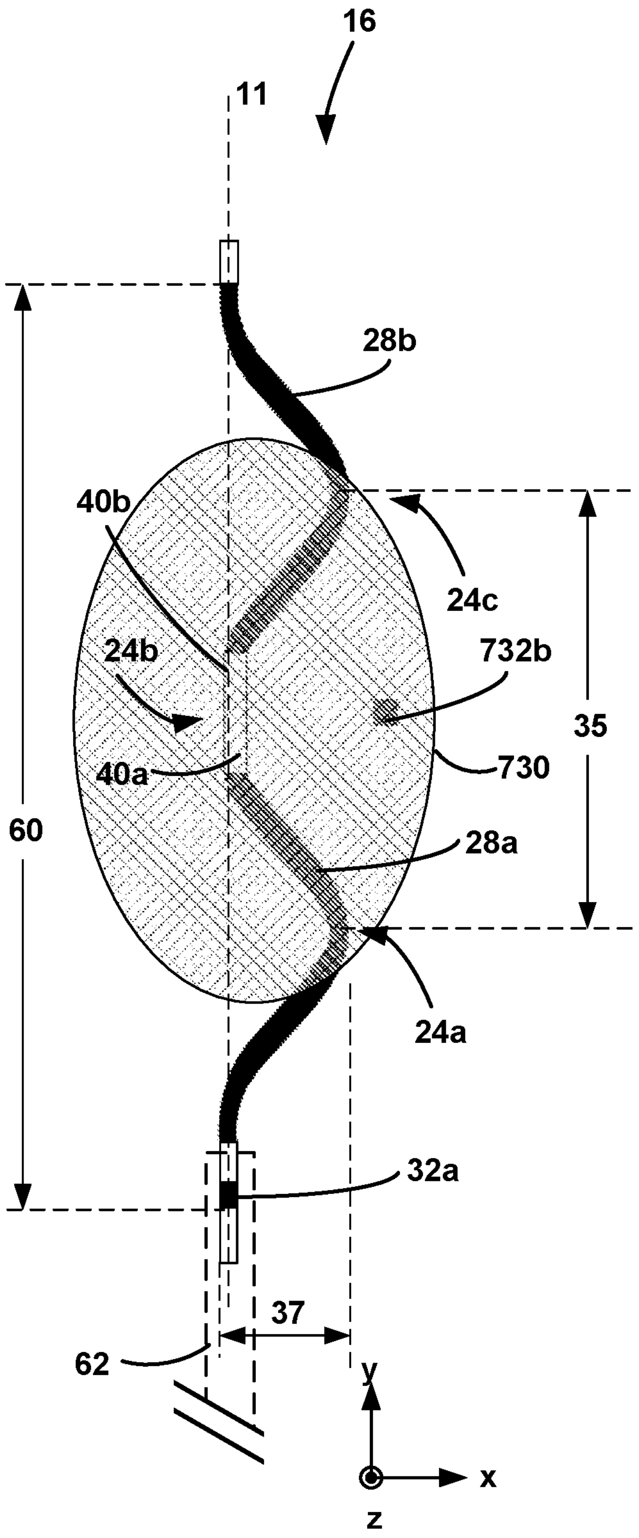
FIG. 7 is a conceptual diagram illustrating an anterior view of a distal portion of another example implantable medical lead and another example shield in a deployed configuration.

FIG. 7 is a conceptual diagram illustrating an anterior view of an example distal portion 16 of example implantable medical lead 10 and another example shield 730 in a deployed configuration. Lead 10 and distal portion 16 may be as described above at FIGS. 2-4. Shield 730 may be substantially similar to any of shields 30, 530, and/or 630 and pacing/sense electrode 732*b* may be substantially similar to pacing/sense electrode 32*b* described above, but pacing/sense electrode 732*b* may be configured to extend laterally with shield 730. For example, pacing/sense electrode 732*b* may be bonded and/or attached to shield 730.

Shield 730 may be an inflatable shield configured to move pacing/sense electrode 732*b* laterally upon inflation. In some examples, shield 730 may be configured to move pacing/sense electrode 732*b* to improve a sensing vector, improve delivery of pacing pulses, reduce delivery of electrical fields at a position with patient 12, and the like. In some examples, shield 730 may be configured to allow a cable to connect with pacing/sense electrode 732*b* once laterally shifted in the deployed configuration. e.g., shield 730 may include a button hole, aperture, rivet, or any suitable structure for allowing a cable to extend from distal portion 16 to pacing/sense electrode 732*b* via shield 730. In some examples, distal portion 16 may include pacing/sense electrode 32*b*, and shield 730 may include pacing/sense electrode 732*b*, e.g., as an additional pacing/sense electrode. In some examples, shield 730 may include a plurality of laterally extended pacing/sense electrodes 732*b*, e.g., extended in the longitudinal direction, the width direction, and/or any other suitable direction. In some examples, shield 730 may be configured to be attached and/or bonded to distal portion 16 along its entire length, e.g., length 60.

Figure 8:
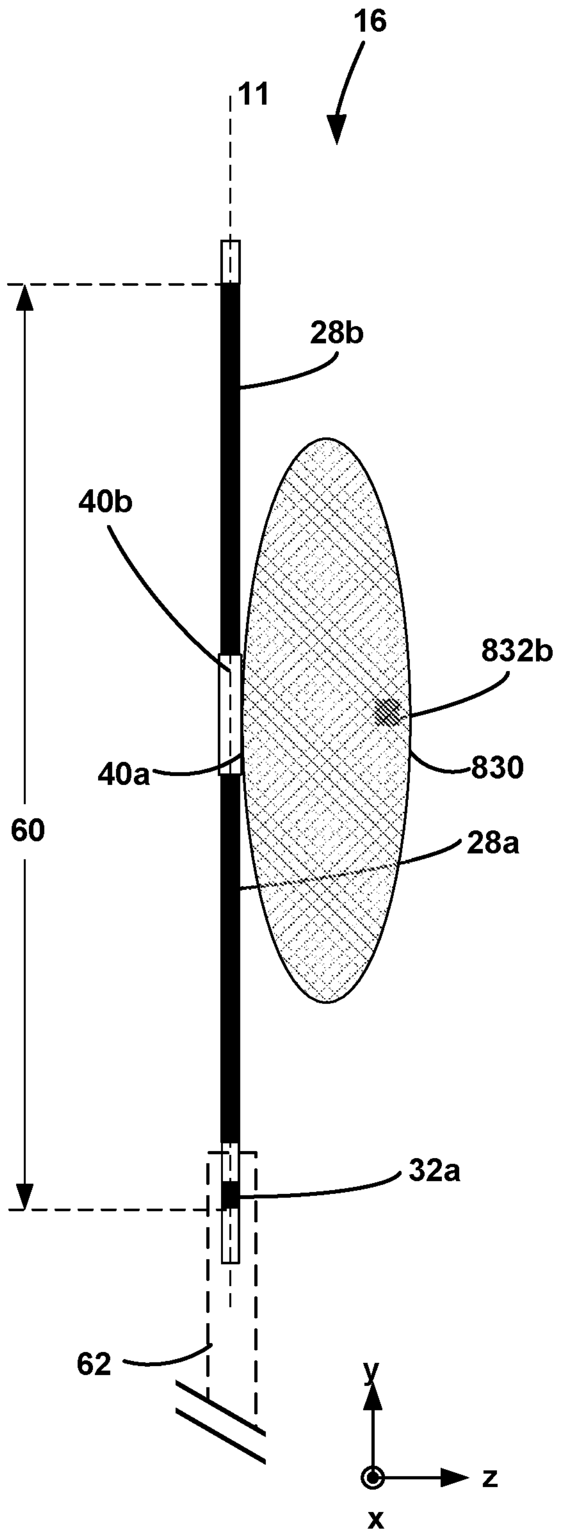
FIG. 8 is a conceptual diagram illustrating a lateral view of a distal portion of another example implantable medical lead and another example shield in a deployed configuration.

FIG. 8 is a conceptual diagram illustrating a lateral view of an example distal portion 16 of example implantable medical lead 10 and another example shield 830 in a deployed configuration. Lead 10 and distal portion 16 may be as described above at FIGS. 2-4. Pacing/sense electrode 832*b* and shield 830 may be substantially similar to any of shields 30, 530, 630, and/or 730 and pacing/sense electrode 32*b* described above, but pacing/sense electrode 832*b* may be configured to extend posteriorly towards the heart of the patient with shield 830. For example, pacing/sense electrode 832*b* may be bonded and/or attached to shield 830.

Shield 830 may be an inflatable shield configured to move pacing/sense electrode 832*b* posteriorly towards the heart of the patient when expanded, e.g., upon inflation. In some examples, shield 830 may be configured to move pacing/sense electrode 832*b* to improve a sensing vector, improve delivery of pacing pulses, reduce delivery of electrical fields at a position with patient 12, and the like. In some examples, shield 830 may be configured to allow a cable to connect with pacing/sense electrode 832*b* once laterally shifted in the deployed configuration, e.g., shield 830 may include a button hole, aperture, rivet, or any suitable structure for allowing a cable to extend from distal portion 16 to pacing/sense electrode 832*b* via shield 830. In some examples, distal portion 16 may include pacing/sense electrode 32*b*, and shield 830 may include pacing/sense electrode 832*b*, e.g., as an additional pacing/sense electrode. In some examples, shield 830 may include a plurality of laterally extended pacing/sense electrodes 832*b*, e.g., extended in the longitudinal direction, the width direction, and/or any other suitable direction. In some examples, shield 830 may be additionally or alternatively configured to move distal portion 16 towards the heart of patient 12 upon expansion, deployment, and/or inflation. In some examples, shield 830 may be configured to be attached and/or bonded to distal portion 16 along its entire length, e.g., length 60.

Figure 9:
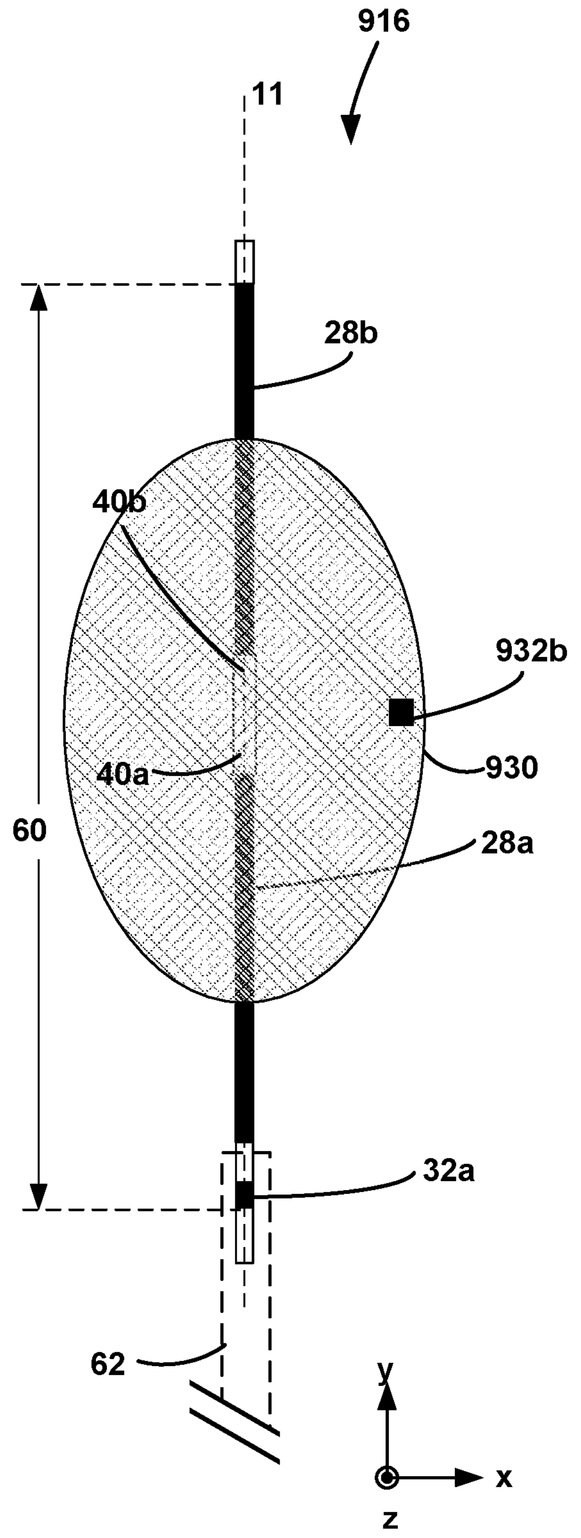
FIG. 9 is a conceptual diagram illustrating an anterior view of an example distal portion of another implantable medical lead and another example shield in a deployed configuration.

FIG. 9 is a conceptual diagram illustrating an anterior view of an example distal portion 916 of example implantable medical lead 10 and another example shield 930 in a deployed configuration. Distal portion 916 and shield 930 may be substantially similar to distal portion 16 and shield 730 and/or 830 described above at FIGS. 7-8, but with a substantially straight distal portion 916, e.g., with electrodes 28 and 32*a* configured to be aligned substantially along a common axis. For example, defibrillation electrodes 28 may be configured to be substantially along a common axis in the deployed configuration, e.g., when shield 830 is expanded and/or inflated.

In the example shown, pacing/sense electrode 932*b* may be substantially similar to pacing/sense electrode 732*b* and/or 832*b* described above, e.g., pacing/sense electrode may be configured to extend laterally and/or posteriorly towards the heart of patient 12 with shield 930. For example, pacing/sense electrode 932*b* may be bonded and/or attached to shield 930.

In some examples, shield 930 may include a plurality of pacing/sense electrodes 932*b* (which may be additionally substantially similar to pacing/sense electrode 32*a*) as well as one or more defibrillation electrodes. Shield 930 may be configured to move any of pacing/sense electrodes 932*b* and/or defibrillation electrodes (not shown) away from the common axis. For example, shield 930 may allow pacing/sense electrodes or defibrillation electrodes to be shifted away from the lead body common axis, e.g., distal portion 916 and/or longitudinal axis 11, while enabling distal portion 916 to be substantially straight, e.g., without an undulating shape. In some examples, shield 930 may be configured to be attached and/or bonded to distal portion 916 along its entire length, e.g., length 60, and may be configured to be tapered at one or both of the distal and proximal ends of distal portion 916, e.g., to enable a smooth transition through introducer 62 and improve removability.

Figure 10:
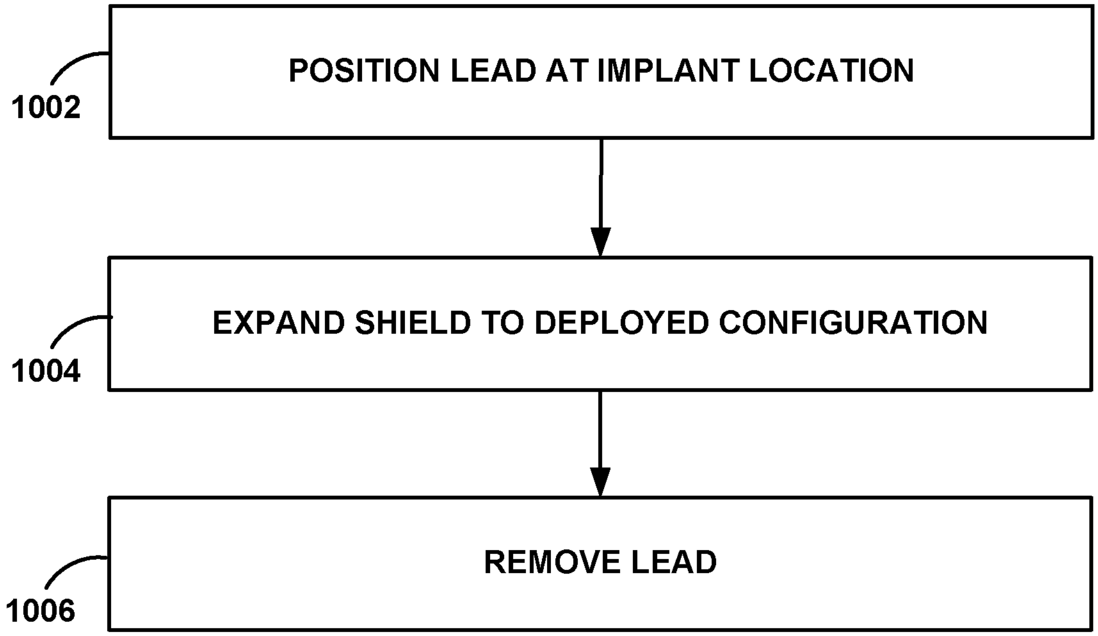
FIG. 10 is a flow diagram illustrating an example technique for implanting an implantable medical lead including a shield.

FIG. 10 is a flow diagram illustrating an example technique for implanting an implantable medical lead including a shield. FIG. 10 is described with respect to implantable medical lead 10, distal portion 16, and shield 30. However, the example technique of FIG. 10 may be used to implant other leads and or shields, such as any lead, distal portion, of shield described herein.

A medical practitioner may position and/or implant distal portion 16 of implantable medical lead 10 into a substernal or other extravascular location using an implant tool (1002). In some examples, distal portion 16 may be loaded into the lumen and packaged in a sterile package prior to the implantation procedure, e.g., by a manufacturer of lead 10 and/or the implant tool. The lumen of the implant tool may be cylindrical, or may otherwise have a profile that matches the outer profile of distal portion 16, e.g., in an undeployed configuration. The undulating configuration of distal portion 16 may be straightened when within the lumen. In one example, the lumen may comprise a sheath. Configurations other than those including a lumen of an implant tool for releasing shield 30 are contemplated by this disclosure.

In some examples, the medical practitioner may introduce the implant tool into the patient via a subxiphoid incision, and advance the implant tool to the extravascular location. Advancement of the tool to the extravascular location may occur before or after implantable medical lead 10 is loaded into the tool. In either case, distal portion 16 of lead 10 is positioned at the extravascular location using the implant tool, e.g., by advancement through the lumen or advancement of the tool while in the lumen. In one embodiment, the implant tool may include a tunneling tool having a rod or other tunneling member and a sheath configured to be placed on the rod. The medical practitioner may removes distal portion 16 of lead 10 from the implant tool to position distal portion 16 at the implantation location and/or site.

The medical practitioner may expand and/or deploy shield 30 from a first shape in the undeployed configuration to a second shape in the deployed configuration (1004). In some examples, the deployed shape of shield 30 may be larger than the undeployed configuration and shield 30 may be asymmetric in the deployed configuration.

In some examples, the medical practitioner may remove distal portion 16 and shield 30 of implantable medical lead 10 using an implant tool (1006). For example, shield 30 may be configured to release from tissue when being removed, and the medical practitioner may advance an introducer, or retract distal portion 16, to compress distal portion 16 and/or shield 30 into a lumen of the introducer.

Figure 11:
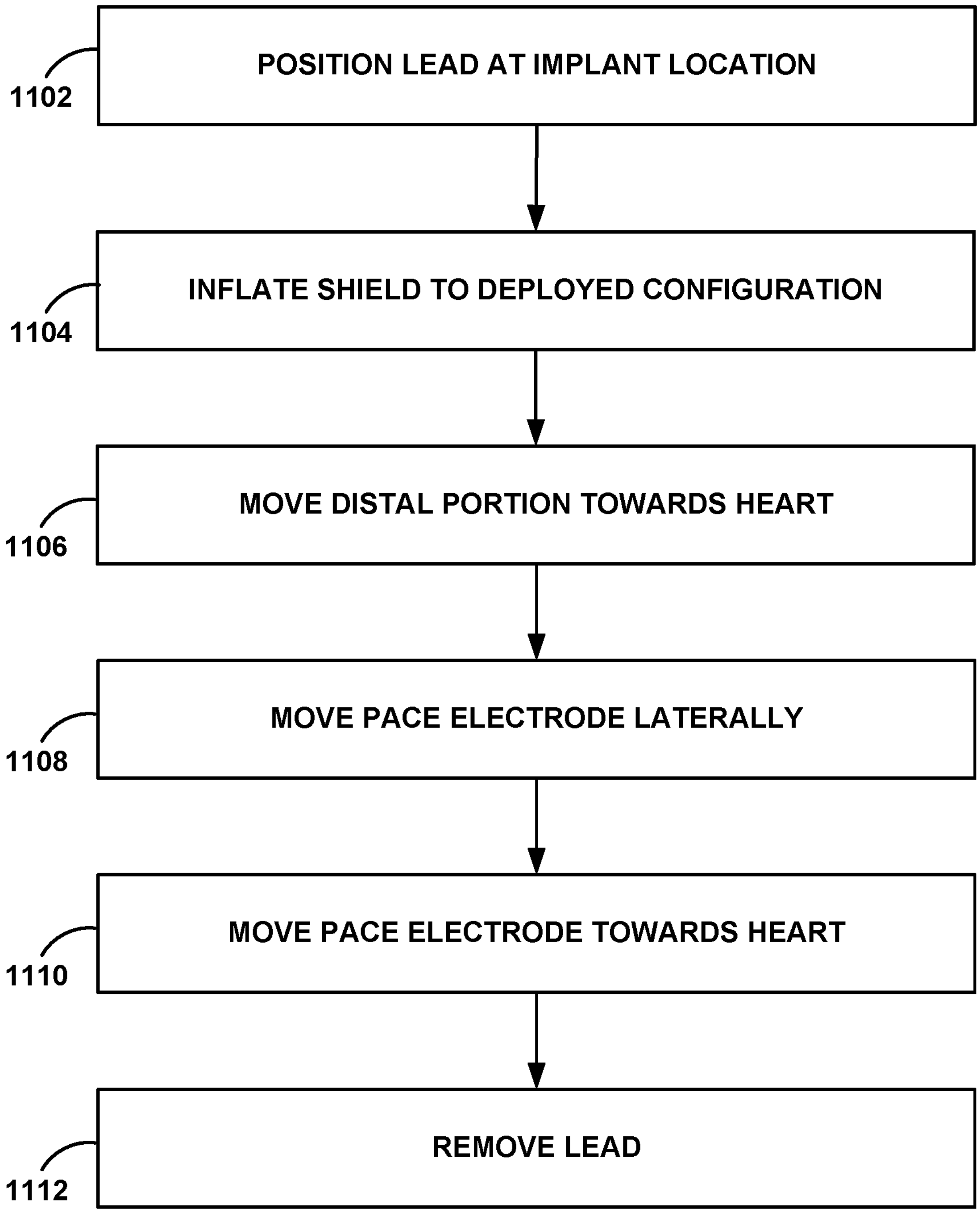
FIG. 11 is a flow diagram illustrating an example technique for implanting an implantable medical lead comprising an inflatable shield.

FIG. 11 is a flow diagram illustrating another example technique for implanting an implantable medical lead including a shield. FIG. 11 is described with respect to implantable medical lead 10, distal portion 16, and shield 730. However, the example technique of FIG. 11 may be used to implant other leads and or shields, such as any lead, distal portion, of shield described herein.

A medical practitioner may position and/or implant distal portion 16 of implantable medical lead 10 into a substernal or other extravascular location using an implant tool (1102), e.g., similar to as described above at (1002). The medical practitioner may inflate shield 730 from a first shape in the undeployed configuration to a second shape in the deployed configuration (1104). In some examples, the deployed shape of shield 730 may be larger than the undeployed configuration.

Shield 730 may move distal portion 16 towards the heart of patient 12 upon inflation (1106). For example, shield 730 may be a balloon positioned anterior to distal portion 16 and may push against anatomy of patient 12 to push distal portion 16 towards the heart. Shield 730 may move a pacing/sense electrode **732*b* laterally upon inflation (1108). For example, pacing/sense electrode 732*b* may be attached and/or bonded to shield 730, and may move laterally away from longitudinal axis 11 upon inflation of shield 730. Shield 730 may move pacing/sense electrode 732*b* posteriorly towards the heart of patient 12 upon inflation of shield 730 (1110). Although 1108 and 1110 are depicted as separate steps, 1108 and 1110 may occur together, e.g., close to or at the same time upon inflation of shield 730**.

In some examples, the medical practitioner may remove distal portion 16 and shield 730 of implantable medical lead 10 using an implant tool (1112). For example, shield 730 may be configured to compress and/or deflate and release from tissue when being removed, and the medical practitioner may advance an introducer, or retract distal portion 16, to compress distal portion 16 and/or shield 730 into a lumen of the introducer.

Figure 12:
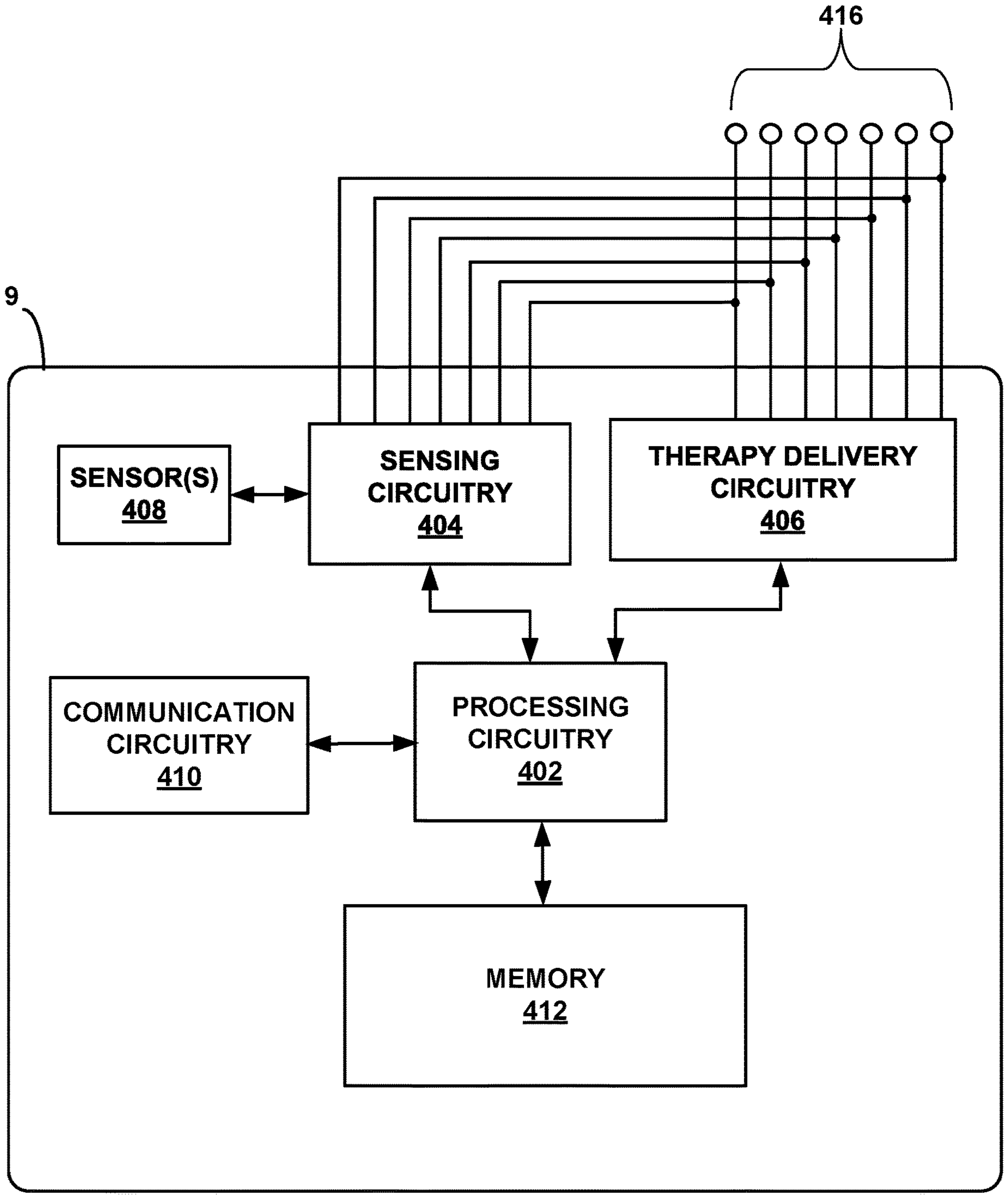
FIG. 12 is a functional block diagram of an example configuration of electronic components of an example ICD.
Figure 13A:
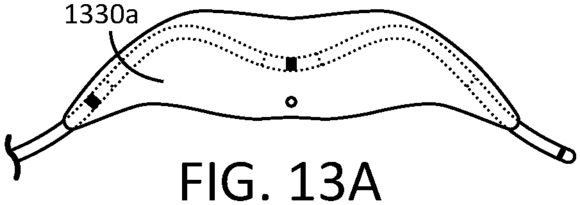
FIGS. 13A-13J are conceptual diagrams each illustrating an anterior view of a distal portion of various example implantable medical leads having various shapes and various example shields having various shapes, each in a deployed configuration.
Figure 13B:
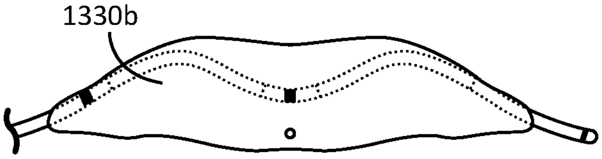
Figure 13C:
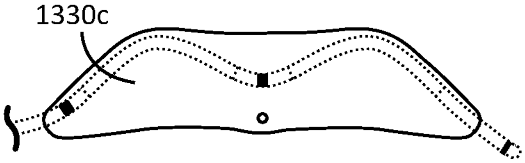
Figure 13D:
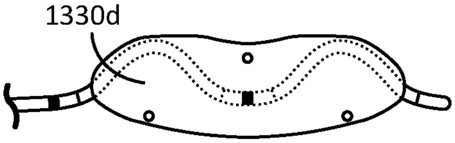
Figure 13E:
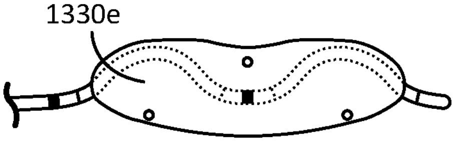
Figure 13F:
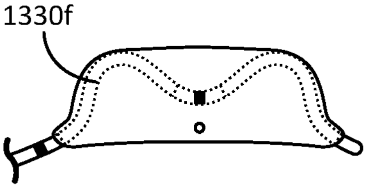
Figure 13G:
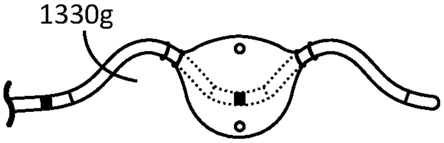
Figure 13H:
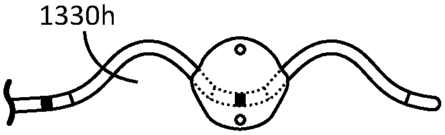
Figure 13I:
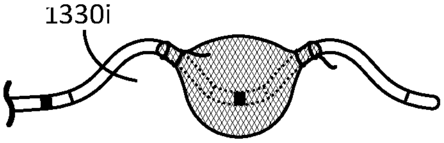
Figure 13J:
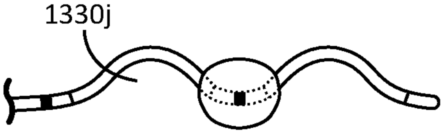

FIG. 12 is a functional block diagram of an example configuration of electronic components and other components of ICD 9. ICD 9 includes a processing circuitry 402, sensing circuitry 404, therapy delivery circuitry 406, sensors 408, communication circuitry 410, and memory 412. In other examples, ICD 9 may include more or fewer components. The described circuitry and other components may be implemented together on a common hardware component or separately as discrete but interoperable hardware or software components. Depiction of different features is intended to highlight different functional aspects and does not necessarily imply that such circuitry and other components must be realized by separate hardware or software components. Rather, functionality associated with one or more circuitries and components may be performed by separate hardware or software components, or integrated within common or separate hardware or software components.

Sensing circuitry 404 may be electrically coupled to some or all of electrodes 416, which may correspond to any of the defibrillation, pace/sense, and housing electrodes described herein. Sensing circuitry 404 is configured to obtain signals sensed via one or more combinations of electrodes 416 and process the obtained signals.

The components of sensing circuitry 404 may be analog components, digital components or a combination thereof. Sensing circuitry 404 may, for example, include one or more sense amplifiers, filters, rectifiers, threshold detectors, analog-to-digital converters (ADCs) or the like. Sensing circuitry 404 may convert the sensed signals to digital form and provide the digital signals to processing circuitry 402 for processing or analysis. For example, sensing circuitry 404 may amplify signals from the sensing electrodes and convert the amplified signals to multi-bit digital signals by an ADC. Sensing circuitry 404 may also compare processed signals to a threshold to detect the existence of atrial or ventricular depolarizations (e.g., P- or R waves) and indicate the existence of the atrial depolarization (e.g., P-waves) or ventricular depolarizations (e.g., R-waves) to processing circuitry 402. As shown in FIG. 12, ICD 9 may additionally include one or more sensors 408, such as one or more accelerometers, which may be configured to provide signals indicative of other parameters of a patient, such as activity or posture, to processing circuitry 402.

Processing circuitry 402 may process the signals from sensing circuitry 404 to monitor electrical activity of heart 26 of patient 12. Processing circuitry 402 may store signals obtained by sensing circuitry 404 as well as any generated EGM waveforms, marker channel data or other data derived based on the sensed signals in memory 412. Processing circuitry 402 may analyze the EGM waveforms and/or marker channel data to detect arrhythmias (e.g., bradycardia or tachycardia). In response to detecting the cardiac event, processing circuitry 402 may control therapy delivery circuitry 406 to deliver the desired therapy to treat the cardiac event, e.g., defibrillation shock, cardioversion shock, ATP, post shock pacing, or bradycardia pacing.

Therapy delivery circuitry 406 is configured to generate and deliver electrical therapy to heart 26. Therapy delivery circuitry 406 may include one or more pulse generators, capacitors, and/or other components capable of generating and/or storing energy to deliver as pacing therapy, defibrillation therapy, cardioversion therapy, cardiac resynchronization therapy, other therapy or a combination of therapies.

In some instances, therapy delivery circuitry 406 may include a first set of components configured to provide pacing therapy and a second set of components configured to provide defibrillation therapy. In other instances, therapy delivery circuitry 406 may utilize the same set of components to provide both pacing and defibrillation therapy. In still other instances, therapy delivery circuitry 406 may share some of the defibrillation and pacing therapy components while using other components solely for defibrillation or pacing. Processing circuitry 402 may control therapy delivery circuitry 406 to deliver the generated therapy to heart 26 via one or more combinations of electrodes 416. Although not shown in FIG. 10, ICD 9 may include switching circuitry configurable by processing circuitry 402 to control which of electrodes 416 is connected to therapy delivery circuitry 406 and sensing circuitry 404.

Communication circuitry 410 includes any suitable hardware, firmware, software or any combination thereof for communicating with another device, such as a clinician programmer, a patient monitoring device, or the like. For example, communication circuitry 410 may include appropriate modulation, demodulation, frequency conversion, filtering, and amplifier components for transmission and reception of data with the aid of an antenna.

The various components of ICD 9 may include any one or more processors, controllers, digital signal processors (DSPs), application specific integrated circuits (ASICs), field-programmable gate arrays (FPGAs), or equivalent discrete or integrated circuitry, including analog circuitry, digital circuitry, or logic circuitry. Processing circuitry 402 may include fixed function circuitry and/or programmable processing circuitry. The functions attributed to processing circuitry 402 herein may be embodied as software, firmware, hardware or any combination thereof.

Memory 412 may include computer-readable instructions that, when executed by processing circuitry 402 or other components of ICD 9, cause one or more components of ICD 9 to perform various functions attributed to those components in this disclosure. Memory 412 may include any volatile, non-volatile, magnetic, optical, or electrical media, such as a random-access memory (RAM), read-only memory (ROM), non-volatile RAM (NVRAM), static non-volatile RAM (SRAM), electrically-erasable programmable ROM (EEPROM), flash memory, or any other non-transitory computer-readable storage media.

FIGS. 13A-13J are conceptual diagrams each illustrating an anterior view of distal portions of various example implantable medical leads having various shapes and various example shields having various shapes and dimensions (e.g., having different surface areas), each in a deployed configuration covering different areas of the distal portion of the implantable medical lead. In the example shown in FIG. 13I, shield 1330*i* is attached to the distal portion of the medical lead via sutures. In some examples, the sutures may be configured to dissolve and/or be absorbed by the patient, e.g., over a period of time. For example, the sutures may attach shield 1330*i* to the distal portion during delivery and deployment, and the subsequently be dissolved and/or absorbed by the patient, and the shield may no longer be attached to the distal portion. If the medical lead is removed and/or extracted from the patient, shield 1330*i* may be configured to be removed separately from the medical lead.

In the examples shown in FIGS. 13A-13H and 13J, shields 1330*a*-1330*h* and 1330*j* may be bonded to the distal portion along the entire length of the undulating shape of the distal portion within the length/width extent of the shield and configured to prevent ingrowth of tissue between the shield and the lead. For example, the bonding along the entire length of each of shields may prevent tissue from growing around at least a portion of the circumference of the distal portions that is bonded to shields 1330*a*-1330*h* and 1330*j*. In some examples, the bonding may improve the releasability of the distal portion and/or medical lead during removal and/or extraction of the medical lead, e.g., via preventing ingrowth of tissue between shields 1330*a*-1330*h* and 1330*j* and each respective distal portion.

Figure 14:
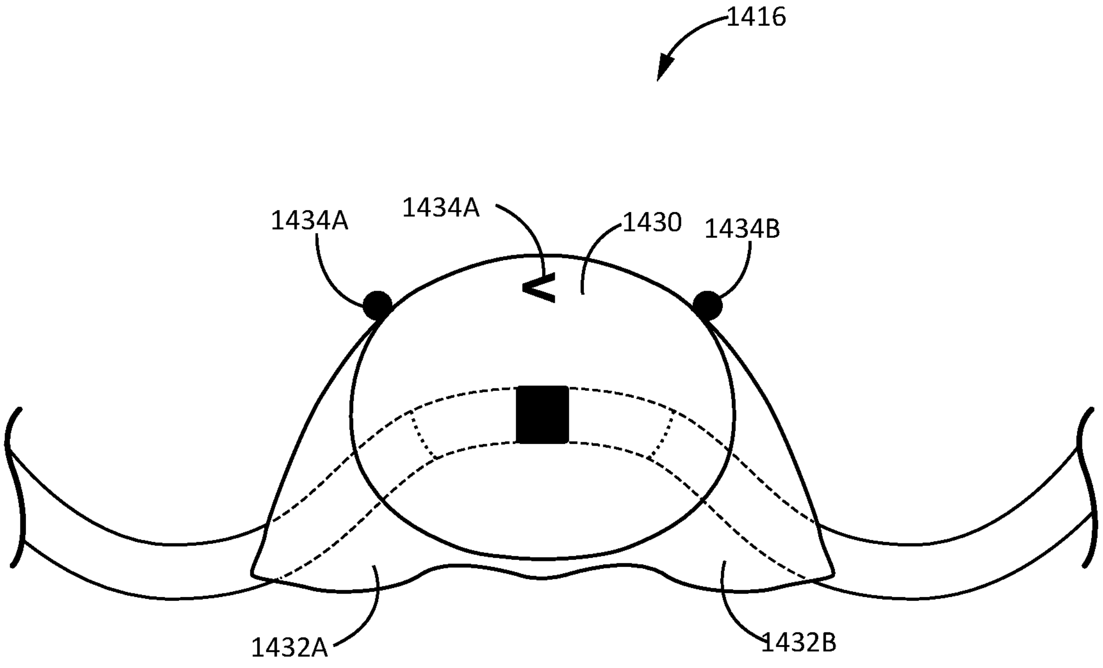
FIG. 14 is a conceptual diagram illustrating an anterior view of a distal portion of another example implantable medical lead and another example shield including a taper and in a deployed configuration.

FIG. 14 is a conceptual diagram illustrating an anterior view of a distal portion 1416 of another example implantable medical lead and another example shield 1430 including tapered portions 1432A and 1432B in a deployed configuration. In some examples, shield 1430 and tapered portions 1432A and 1432B are configured to improve transition through a delivery tool lumen during deployment/implantation, and to improve extraction of distal portion 1416 (and/or the medical lead), e.g., via providing a smooth shield transition to reduce catching of the shield on a catheter and/or sheath when distal portion 1416 is retracted/extracted.

In some examples, distal portion 1416 may include one or more markers. In the example shown, shield 1430 includes markers 1434*a* and 1434*b*. In some examples, markers 1434*a* and 1434*b* may be positioned on shield 1430, and may be configured to indicate a position, an orientation, and/or a "distortion" or proper deployment of shield 1430 during or after implantation. For example, markers 1434*a* and 1434*b* may be configured to indicate whether shield 1430 is improperly deployed, e.g., whether at least a portion of shield 1430 is folded over or otherwise improperly deployed, or whether shield 1430 is properly deployed.

In some examples, shield 1430 may include a single marker, e.g., marker 1434*c*. Marker 1424*c* may be positioned on shield 1430, and may be configured to indicate a position, an orientation, and/or a "distortion" or proper deployment of shield 1430 during or after implantation, e.g., similar to markers 1434*a* and 1434*b* described above, but as a single marker. For example, marker 1434*c* may have a particular shape and/or symmetry or asymmetry such that marker 1434*c* is configured to indicate whether shield 1430 is improperly deployed, e.g., to indicate whether at least a portion of shield 1430 is folded over or otherwise improperly deployed, or whether shield 1430 is properly deployed. For example, marker 1434*c* may have a substantially circular shape, which may have an aspect ratio change, or be distorted, to an elliptical shape, or some other shape, if shield 1430 is improperly deployed (e.g., having at least a portion folder over or not fully inflated). In the example shown, marker 1434*c* is a "chevron" or "carrot" shape. In some examples, any or all of markers 1434*a*, 1434*b*, and 1434*c* may be radiopaque.

The following examples are described herein.

Example 1: An implantable medical lead including: a first defibrillation electrode and a second defibrillation electrode, the first and second defibrillation electrodes configured to deliver first electrical therapy; a pace electrode disposed longitudinally between the first defibrillation electrode and the second defibrillation electrode, the pace electrode configured to deliver second electrical therapy comprising pacing pulses; and a shield disposed at least over a portion of an outer surface of the pace electrode and extending laterally away from the pace electrode, wherein the shield comprises an asymmetric shape about a longitudinal axis of the shield, wherein the shield is configured to impede an electric field of at least one of the first and second electrical therapies in a direction away from a heart of the patient.

Example 2: The implantable medical lead of example 1, wherein the shield comprises a single layer of a substantially flat and biocompatible material.

Example 3: The implantable medical lead of example 1 or example 2, wherein the longitudinal axis of the shield is along a length of a distal portion of the implantable medical lead comprising the pace electrode and the first and second defibrillation electrodes, wherein the asymmetric shape of the shield is substantially elliptical having a major axis substantially aligned with the longitudinal axis of the shield.

Example 4: The implantable medical lead of example 3, wherein the asymmetric shape of the shield is a kidney bean shape having an indent at one side of the elliptical shape.

Example 5: The implantable medical lead of any one of examples 1 through 4, wherein the shield is configured to self-deploy.

Example 6: The implantable medical lead of example 5, wherein the shield is configured to be compressed to a first shape for implantation of the implantable medical lead and to elastically expand to the asymmetric shape when the implantable medical lead is implanted.

Example 7: The implantable medical lead of example 6, wherein a length of the shield expanded to the asymmetric shape is greater than a length of the pace electrode, wherein a width of the shield expanded to the asymmetric shape is greater than a width of the pace electrode.

Example 8: The implantable medical lead of any one of examples 6 and 7, wherein a distal portion of the implantable medical lead comprises the pace electrode and the first and second defibrillation electrodes, wherein a length of the shield expanded to the asymmetric shape is greater than a length of the distal portion of the implantable medical lead, wherein a width of the shield expanded to the asymmetric shape is greater than a width of the distal portion of the implantable medical lead.

Example 9: The implantable medical lead of example 8, wherein the distal portion of the implantable medical lead defines an undulating configuration including a first peak extending in a first direction, a second peak extending in the first direction, and a third peak, between the first peak and the second peak, extending in a second direction opposite the first direction, and wherein at least a portion of the first defibrillation electrode is disposed on the first peak, at least a portion of the second defibrillation electrode is disposed on the second peak, and at least a portion of the pace electrode is disposed on the third peak.

Example 10: The implantable medical lead of example 9, wherein the distal portion of the implantable medical lead is configured to deform from the undulating configuration to a second configuration configured to allow the distal portion of the implantable medical lead to be deployable via a delivery tool and to deploy to the undulating configuration when deployed, wherein the shield is configured to be deployed with the distal portion of the implantable medical lead in the first shape via the delivery tool and to deploy to the asymmetric shape when deployed.

Example 11: The implantable medical lead of any one of examples 1 through 10, wherein a distal portion of the implantable medical lead comprises the pace electrode and the first and second defibrillation electrodes, wherein the shield is configured to be an elastic membrane web bonded to the distal portion along the entire length of the distal portion.

Example 12: The implantable medical lead of example 11, wherein the membrane web comprises a polyurethane elastomer.

Example 13: The implantable medical lead of any one of examples 1 through 12, wherein the shield is configured to release from tissue when being removed.

Example 14: The implantable medical lead of any one of examples 1 through 13, wherein the shield extends at least 10 millimeters from the pace electrode in any lateral direction.

Example 15: The implantable medical lead of any one of examples 1 through 14, wherein the shield is tapered and bonded at each of the first and second defibrillation electrodes.

Example 16: The implantable medical lead of any one of examples 1 through 15, wherein the shield is configured to contract into an introducer during removal of the implantable medical lead.

Example 17: A method including: positioning an implantable medical lead at an implant location within a patient, wherein the implantable medical lead comprises: a first defibrillation electrode and a second defibrillation electrode, the first and second defibrillation electrodes configured to deliver antitachyarrhythmia shocks; a pace electrode disposed longitudinally between the first defibrillation electrode and the second defibrillation electrode, the pace electrode configured to deliver a pacing pulse that generates an electric field proximate to the pace electrode; and a shield configured to be disposed at least over a portion of an outer surface of the pace electrode and extending laterally away from the pace electrode in a deployed configuration, wherein the shield comprises an asymmetric shape about a longitudinal axis of the shield in the deployed configuration, wherein the shield is configured to impede an electric field of at least one of the first and second electrical therapies in a direction away from a heart of the patient in the deployed configuration; and expanding, via deploying the implantable medical lead, the shield from a first shape to the asymmetric shape in the deployed configuration.

Example 18: The method of example 17, wherein the shield comprises a shape having atraumatic edges.

Example 19: The method of example 17 or example 18, wherein the shield comprises a single layer of a substantially flat and biocompatible material.

Example 20: The method of any one of examples 17 through 19, wherein the longitudinal axis of the shield is along a length of a distal portion of the implantable medical lead comprising the pace electrode and the first and second defibrillation electrodes, wherein the asymmetric shape of the shield is substantially elliptical having a major axis substantially aligned with the longitudinal axis of the shield.

Example 21: The method of example 20, wherein the asymmetric shape of the shield is a kidney bean shape having an indent at one side of the elliptical shape.

Example 22: The method of any one of examples 17 through 21, wherein the shield is configured to be compressed to the first shape in an undeployed configuration, wherein the first shape configured to be compatible with a delivery tool configured to deploy the implantable medical lead, wherein the shield is configured to elastically self-expand to the asymmetric shape upon deployment of the implantable medical lead.

Example 23: The method of any one of examples 17 through 22, wherein a length of the shield expanded to the asymmetric shape is greater than a length of the pace electrode, wherein a width of the shield expanded to the second shape is greater than a width of the pace electrode.

Example 24: The method of any one of examples 17 through 22, wherein a distal portion of the implantable medical lead comprises the pace electrode and the first and second defibrillation electrodes, wherein a length of the shield expanded to the asymmetric shape is greater than a length of the distal portion, wherein a width of the shield expanded to the asymmetric shape is greater than a width of the distal portion.

Example 25: The method of any one of examples 17 through 24, further including: removing, via an introducer, the implantable medical lead, wherein the shield is configured to release from tissue when being removed.

Example 26: The method of example 25, wherein the shield is tapered and bonded at each of the first and second defibrillation electrodes and is configured to contract into the introducer during removal of the implantable medical lead.

Example 27: A system including: an implantable medical lead including: a first defibrillation electrode and a second defibrillation electrode, the first and second defibrillation electrodes configured to deliver first electrical therapy; a pace electrode disposed longitudinally between the first defibrillation electrode and the second defibrillation electrode, the pace electrode configured to deliver second electrical therapy comprising pacing pulses; and a shield comprising a substantially flat and single-layered biocompatible material configured to be attached to the implantable medical lead and in a first shape in an undeployed configuration, wherein the shield is configured to be compatible with a delivery tool in the first shape, wherein the shield is configured to be in an asymmetric shape about a longitudinal axis of the shield and disposed over a portion of an outer surface of the pace electrode and extending laterally away from the pace electrode in a deployed configuration, wherein the asymmetric shape, wherein the shield is configured to impede an electric field of at least one of the first and second electrical therapies in a direction away from a heart of the patient in the deployed configuration.

Example 28: An implantable medical lead including: a first defibrillation electrode and a second defibrillation electrode, the first and second defibrillation electrodes configured to deliver first electrical therapy; a pace electrode disposed longitudinally between the first defibrillation electrode and the second defibrillation electrode, the pace electrode configured to deliver a pacing pulse that generates an electric field proximate to the pace electrode; and an inflatable shield disposed at least over a portion of an outer surface of the pace electrode, wherein the inflatable shield is configured to extend laterally away from the pace electrode upon inflation, wherein the inflatable shield is configured to impede an electric field of at least one of the first and second the electrical therapies in a direction away from a heart of the patient.

Example 29: The medical device system of example 28, wherein the inflatable shield is configured to inflate with at least one of a gas or a liquid.

Example 30: The implantable medical lead of example 29, wherein the implantable medical lead includes a lumen therein, the lumen coupled with the inflatable shield and configured to provide the gas or the liquid to and from the inflatable shield.

Example 31: The implantable medical lead of any one of examples 28 through 30, wherein a length of the inflatable shield, upon inflation, is greater than a length of the pace electrode, wherein a width of the inflatable shield, upon inflation, is greater than a width of the pace electrode.

Example 32: The implantable medical lead of any one of examples 28 through 31, wherein a distal portion of the implantable medical lead comprises the pace electrode and the first and second defibrillation electrodes, wherein a length of the inflatable shield, upon inflation, is greater than a length of the distal portion, wherein a width of the inflatable shield, upon inflation, is greater than a width of the distal portion.

Example 33: The implantable medical lead of any one of examples 28 through 32, wherein the inflatable shield is electrically insulative.

Example 34: The implantable medical lead of any one of examples 28 through 33, wherein the inflatable shield comprises two layers of a polyurethane.

Example 35: The implantable medical lead of any one of examples 28 through 34, wherein a distal portion of the implantable medical lead comprises the pace electrode and the first and second defibrillation electrodes, wherein the inflatable shield is configured to move the distal portion towards the heart of the patient upon inflation.

Example 36: The implantable medical lead of any one of examples 28 through 35, wherein the pace electrode is located on the inflatable shield, and the inflatable shield is configured to move the pace electrode laterally upon inflation.

Example 37: The implantable medical lead of example 36, wherein the first and second defibrillation electrodes and the pace electrode are configured to be aligned substantially along a common axis when the inflatable shield is deflated.

Example 38: The implantable medical lead of any one of examples 28 through 37, wherein the balloon shield is configured to move the pace electrode posteriorly towards the heart of the patient when expanded from the first shape to the second shape.

Example 39: A method including: positioning an implantable medical lead at an implant location within a patient, wherein the implantable medical lead comprises: a first defibrillation electrode and a second defibrillation electrode, the first and second defibrillation electrodes configured to deliver first electrical therapy; a pace electrode disposed longitudinally between the first defibrillation electrode and the second defibrillation electrode, the pace electrode configured to deliver a pacing pulse that generates an electric field proximate to the pace electrode; and an inflatable shield disposed at least over a portion of an outer surface of the pace electrode, wherein the inflatable shield is configured to extend laterally away from the pace electrode in an inflated shape upon inflation, wherein the inflatable shield is configured to impede an electric field of at least one of the first and second the electrical therapies in a direction away from a heart of the patient; and inflating the inflatable shield from a deflated shape to the inflated shape.

Example 40: The method of example 39, further comprising inflating the inflatable shield with at least one of a gas or a liquid, wherein the implantable medical lead includes a lumen therein, the lumen coupled with the balloon shield and configured to provide the gas or the liquid to and from the inflatable shield.

Example 41: The method of example 39 or example 40, wherein a length of the inflatable shield, upon inflation, is greater than a length of the pace electrode, wherein a width of the inflatable shield, upon inflation, is greater than a width of the pace electrode.

Example 42: The method of any one of examples 39 through 41, wherein a distal portion of the implantable medical lead comprises the pace electrode and the first and second defibrillation electrodes, wherein a length of the inflatable shield, upon inflation, is greater than a length of the distal portion, wherein a width of the inflatable shield, upon inflation, is greater than a width of the distal portion.

Example 43: The method of any one of examples 39 through 42, wherein the inflatable shield is electrically insulative, wherein the inflatable shield comprises two layers of a polyurethane.

Example 44: The method of any one of examples 39 through 43, wherein a distal portion of the implantable medical lead comprises the pace electrode and the first and second defibrillation electrodes, the method further including: moving, via inflating the inflatable shield, the distal portion towards the heart of the patient.

Example 45: The method of any one of examples 39 through 44, further including: moving, via inflating the inflatable shield, the pace electrode laterally.

Example 46: The method of any one of examples 39 through 45, wherein the first and second defibrillation electrodes and the pace electrode are configured to be aligned substantially along a common axis when the inflatable shield is deflated.

Example 47: The method of any one of examples 39 through 46, wherein the inflatable shield is configured to move the pace electrode posteriorly towards the heart of the patient upon inflation.

Example 48: A system including: an implantable medical lead including: a first defibrillation electrode and a second defibrillation electrode, the first and second defibrillation electrodes configured to deliver first electrical therapy; a pace electrode disposed between the first defibrillation electrode and the second defibrillation electrode, the pace electrode configured to deliver second electrical therapy comprising pacing pulses; and a lead body defining a lumen configured to guide a needle; an inflatable shield disposed at least over a portion of an outer surface of the pace electrode, wherein the inflatable shield is configured to extend laterally away from the pace electrode upon inflation, wherein the inflatable shield is configured to impede an electric field of at least one of the first and second the electrical therapies in a direction away from a heart of the patient; and a septum between the lumen and the inflatable shield, the septum configured to form a seal about the needle, wherein the needle is configured to provide at least one of a gas or a liquid to inflate the inflatable shield.

The leads and systems described herein may be used at least partially within the substernal space, e.g., within anterior mediastinum of patient, to provide an extravascular ICD system. An implanter (e.g., physician) may implant the distal portion of the lead intra-thoracically using any of a number of implant tools, e.g., tunneling rod, sheath, or other tool that can traverse the diagrammatic attachments and form a tunnel in the substernal location. For example, the implanter may create an incision near the center of the torso of the patient, e.g., and introduce the implant tool into the substernal location via the incision. The implant tool is advanced from the incision superior along the posterior of the sternum in the substernal location. The distal portion of the lead is introduced into the tunnel via implant tool (e.g., via a sheath). As the distal portion is advanced through the substernal tunnel, the distal portion is relatively straight. The pre-formed or shaped undulating configuration is flexible enough to be straightened out while routing the lead through a sheath or other lumen or channel of the implant tool. Once the distal portion is in place, the implant tool is withdrawn toward the incision and removed from the body of the patient while leaving the lead in place along the substernal path. As the implant tool is withdrawn, the distal end of the lead takes on its pre-formed undulating configuration, and the shield transitions to its deployed configuration.

In some examples, rather than extending in a superior direction along the sternum, the distal portion of the lead may be oriented orthogonal or otherwise transverse to the sternum and/or inferior to the heart. In such examples, the lead may include one or more shields that cover a portion of an outer surface of one or more electrodes, e.g., an anterior and/or inferior portion, according to any of the examples described herein. Such shield(s) may impede an electrical field in a direction away from the heart, which may be an anterior and/or inferior direction.

It will be appreciated by persons skilled in the art that the present application is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the application, which is limited only by the following claims.

What is claimed is:

1. An implantable medical lead comprising:

a first defibrillation electrode and a second defibrillation electrode, the first and second defibrillation electrodes configured to deliver first electrical therapy;

a pace electrode disposed longitudinally between the first defibrillation electrode and the second defibrillation electrode, the pace electrode configured to deliver a pacing pulse that generates an electric field proximate to the pace electrode; and an inflatable shield disposed at least over a portion of an outer surface of the pace electrode, wherein the inflatable shield is configured to extend laterally away from the pace electrode upon inflation, wherein the inflatable shield is configured to impede an electric field of at least one of the first electrical therapy or a second electrical therapy in a direction away from a heart of a patient.

2. The implantable medical lead of claim 1, wherein the inflatable shield is configured to inflate with at least one of a gas or a liquid.

3. The implantable medical lead of claim 2, wherein the implantable medical lead includes a lumen therein, the lumen coupled with the inflatable shield and configured to provide the gas or the liquid to and from the inflatable shield.

4. The implantable medical lead of claim 1, wherein a length of the inflatable shield, upon inflation, is greater than a length of the pace electrode, wherein a width of the inflatable shield, upon inflation, is greater than a width of the pace electrode.

5. The implantable medical lead of claim 1, wherein a distal portion of the implantable medical lead comprises the pace electrode and the first and second defibrillation electrodes, wherein a length of the inflatable shield, upon inflation, is greater than a length of the distal portion, wherein a width of the inflatable shield, upon inflation, is greater than a width of the distal portion.

6. The implantable medical lead of claim 1, wherein the inflatable shield is electrically insulative.

7. The implantable medical lead of claim 1, wherein the inflatable shield comprises two layers of a polyurethane.

8. The implantable medical lead of claim 1, wherein a distal portion of the implantable medical lead comprises the pace electrode and the first and second defibrillation electrodes, wherein the inflatable shield is configured to move the distal portion towards the heart of the patient upon inflation.

9. The implantable medical lead of claim 1, wherein the pace electrode is located on the inflatable shield, and the inflatable shield is configured to move the pace electrode laterally upon inflation.

10. The implantable medical lead of claim 9, wherein the first and second defibrillation electrodes and the pace electrode are configured to be aligned along a common axis when the inflatable shield is deflated.

11. The implantable medical lead of claim 1, wherein the inflatable shield is configured to move the pace electrode posteriorly towards the heart of the patient when expanded from a first shape to a second shape.

12. A system comprising:

an implantable medical lead comprising:

a first defibrillation electrode and a second defibrillation electrode, the first and second defibrillation electrodes configured to deliver first electrical therapy;

a pace electrode disposed between the first defibrillation electrode and the second defibrillation electrode, the pace electrode configured to deliver second electrical therapy comprising pacing pulses; and a lead body defining a lumen configured to guide a needle;

an inflatable shield disposed at least over a portion of an outer surface of the pace electrode, wherein the inflatable shield is configured to extend laterally away from the pace electrode upon inflation, wherein the inflatable shield is configured to impede an electric field of at least one of the first and second the electrical therapies in a direction away from a heart of a patient; and a septum between the lumen and the inflatable shield, the septum configured to form a seal about the needle, wherein the needle is configured to provide at least one of a gas or a liquid to inflate the inflatable shield.

13. A method comprising:

positioning an implantable medical lead at an implant location within a patient, wherein the implantable medical lead comprises:

a first defibrillation electrode and a second defibrillation electrode, the first and second defibrillation electrodes configured to deliver first electrical therapy;

a pace electrode disposed longitudinally between the first defibrillation electrode and the second defibrillation electrode, the pace electrode configured to deliver a pacing pulse that generates an electric field proximate to the pace electrode; and an inflatable shield disposed at least over a portion of an outer surface of the pace electrode, wherein the inflatable shield is configured to extend laterally away from the pace electrode in an inflated shape upon inflation, wherein the inflatable shield is configured to impede an electric field of at least one of the electrical therapy or a second electrical therapy in a direction away from a heart of the patient; and inflating the inflatable shield from a deflated shape to the inflated shape.

14. The method of claim 13, further comprising: inflating the inflatable shield with at least one of a gas or a liquid, wherein the implantable medical lead comprises a lumen therein, the lumen coupled with the inflatable shield and configured to provide the gas or the liquid to and from the inflatable shield.

15. The method of claim 13, wherein a length of the inflatable shield, upon inflation, is greater than a length of the pace electrode, wherein a width of the inflatable shield, upon inflation, is greater than a width of the pace electrode.

16. The method of claim 13, wherein a distal portion of the implantable medical lead comprises the pace electrode and the first and second defibrillation electrodes, wherein a length of the inflatable shield, upon inflation, is greater than a length of the distal portion, wherein a width of the inflatable shield, upon inflation, is greater than a width of the distal portion.

17. The method of claim 13, wherein the inflatable shield is electrically insulative, wherein the inflatable shield comprises two layers of a polyurethane.

18. The method of claim 13, wherein a distal portion of the implantable medical lead comprises the pace electrode and the first and second defibrillation electrodes, the method further comprising:

moving, via inflating the inflatable shield, the distal portion towards the heart of the patient.

19. The method of claim 13, further comprising:

moving, via inflating the inflatable shield, the pace electrode laterally.

20. The method of claim 13, wherein the first and second defibrillation electrodes and the pace electrode are configured to be aligned along a common axis when the inflatable shield is deflated, wherein the inflatable shield is configured to move the pace electrode posteriorly towards the heart of the patient upon inflation.

* * * * *